United States Patent
Fang et al.

(10) Patent No.: US 12,171,761 B2
(45) Date of Patent: *Dec. 24, 2024

(54) VILAZODONE INCLUSION COMPLEXES, COMPOSITIONS AND PREPARATION THEREOF

(71) Applicant: Sunshine Lake Pharma Co., Ltd., Guangdong (CN)

(72) Inventors: Dailong Fang, Guangdong (CN); Xiaomiao Qiu, Guangdong (CN); Beiyang Yao, Guangdong (CN); Shuiwang Feng, Guangdong (CN); Xin Huang, Guangdong (CN); Jinsong You, Guangdong (CN); Fangfang Huang, Guangdong (CN)

(73) Assignee: Sunshine Lake Pharma Co., Ltd., Dongguan (CN)

( * ) Notice: Subject to any disclaimer, the term of this patent is extended or adjusted under 35 U.S.C. 154(b) by 977 days.

This patent is subject to a terminal disclaimer.

(21) Appl. No.: 17/183,194

(22) Filed: Feb. 23, 2021

(65) Prior Publication Data

US 2021/0205301 A1 Jul. 8, 2021

Related U.S. Application Data

(63) Continuation-in-part of application No. 16/876,758, filed on May 18, 2020, now Pat. No. 11,517,569, which is a continuation of application No. 16/343,171, filed as application No. PCT/CN2017/108881 on Nov. 1, 2017, now Pat. No. 10,688,090.

(30) Foreign Application Priority Data

Nov. 2, 2016 (CN) .......................... 201610938591.6

(51) Int. Cl.
*A61K 31/496* (2006.01)
*A61K 47/40* (2006.01)
(52) U.S. Cl.
CPC ............ *A61K 31/496* (2013.01); *A61K 47/40* (2013.01)

(58) Field of Classification Search
CPC .............................. A61K 31/496; A61K 47/40
USPC ..................................................... 514/254.09
See application file for complete search history.

(56) References Cited

U.S. PATENT DOCUMENTS

| | | | |
|---|---|---|---|
| 5,532,241 A | 7/1996 | Bottcher et al. | |
| 9,050,328 B2 | 6/2015 | Cen et al. | |
| 10,688,090 B2 * | 6/2020 | Feng | ........................ A61P 25/24 |
| 11,517,569 B2 * | 12/2022 | Feng | ..................... A61K 31/496 |
| 2015/0157575 A1 | 6/2015 | Yang | |

FOREIGN PATENT DOCUMENTS

| | | |
|---|---|---|
| CN | 102860993 | 1/2013 |
| CN | 103211751 | 7/2013 |
| CN | 104116741 | 10/2014 |
| CN | 106540266 | 3/2017 |
| CN | 106667939 | 5/2017 |
| WO | WO-2015019237 | 2/2015 |
| WO | WO-2015019256 | 2/2015 |
| WO | WO-2020119698 | 6/2020 |
| WO | WO-2020119701 | 6/2020 |

OTHER PUBLICATIONS

CN106540266A machine translation (Year: 2017).*
International Search Report of PCT/CN2017/108881 dated Jan. 16, 2018. (3 pages).
Translation of CN 106540266 (Year: 2016).
Written Opinion of PCT/CN2017/108881 dated Jan. 26, 2018. (5 pages).

* cited by examiner

*Primary Examiner* — Yevgeny Valenrod
(74) *Attorney, Agent, or Firm* — Sheppard Mullin Richter & Hampton LLP

(57) ABSTRACT

Disclosed herein are inclusion complexes comprising vilazodone or a pharmaceutically acceptable salt thereof and an inclusion material, compositions and pharmaceutical formulations comprising the inclusion complexes, and methods for preparing the inclusion complexes, compositions or pharmaceutical formulations.

24 Claims, 1 Drawing Sheet

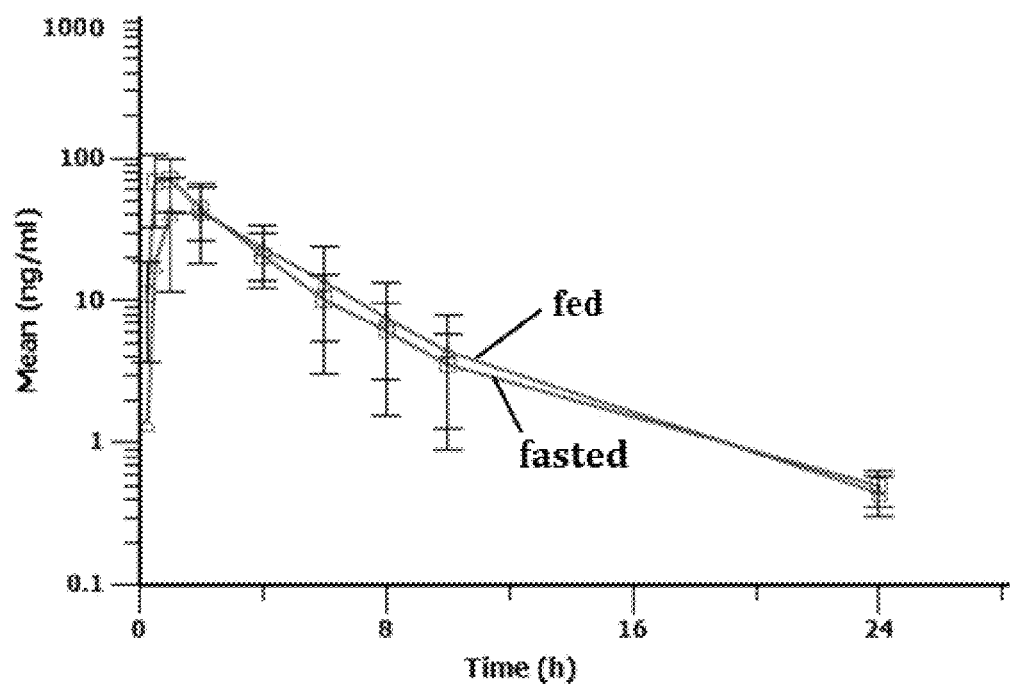

VILAZODONE INCLUSION COMPLEXES, COMPOSITIONS AND PREPARATION THEREOF

CROSS-REFERENCE TO RELATED APPLICATIONS

This application is a continuation-in-part of co-pending U.S. application Ser. No. 16/876,758, filed May 18, 2020, which is a continuation of U.S. application Ser. No. 16/343,171, filed Apr. 18, 2019, now U.S. Pat. No. 10,688,090, which is a U.S. National Stage Application under 35 U.S.C. § 371 of PCT/CN2017/108881, filed Nov. 1, 2017, which application claims the benefit of Chinese Application No. 201610938591.6, filed Nov. 2, 2016, the complete disclosures of which are hereby incorporated by reference.

FIELD OF DISCLOSURE

This disclosure relates to the field of pharmaceutical, in particular, pharmaceutical formulations comprising vilazodone and methods of preparation thereof.

BACKGROUND

Vilazodone, an antidepressant, is a selective serotonin reuptake inhibitor and a 5HT1A receptor partial agonist. VIIBRYD® tablet which contains vilazodone hydrochloride polymorph Form IV was approved by the U.S. Food and Drug Administration (FDA) in 2011 for the treatment of major depressive disorder. The VIIBRYD® label expressly states that VIIBRYD® should be administered with food as administration without food can result in inadequate drug concentrations and may reduce effectiveness.

SUMMARY

In one aspect, provided herein is an inclusion complex comprising an active ingredient and an inclusion material, wherein the active ingredient is vilazodone or a pharmaceutically acceptable salt thereof, and the inclusion material is cyclodextrin or a derivative thereof.

Also provided, in some embodiments, is a composition or a pharmaceutical formulation comprising an active ingredient and an inclusion material, wherein the active ingredient is vilazodone or a pharmaceutically acceptable salt thereof.

In some embodiments, at least about 50% of the active ingredient is contained in inclusion complexes comprising the active ingredient and the inclusion material. In some embodiments, at least about 80% of the active ingredient is contained in inclusion complexes comprising the active ingredient and the inclusion material. In some embodiments, at least about 90% of the active ingredient is contained in the inclusion complexes. In some embodiments, the inclusion material comprises cyclodextrin or a derivative thereof.

In some embodiments, the weight ratio of the active ingredient and the inclusion material is about 1:2.4 to about 1:45.4. In some embodiments, the weight ratio of the active ingredient and the inclusion material is about 1:5 to about 1:45.4. In some embodiments, the weight ratio of the active ingredient and the inclusion material is about 1:6.5 to about 1:45.4. In some embodiments, the weight ratio of the active ingredient and the inclusion material is about 1:8 to about 1:16.5. In some embodiments, the weight ratio of the active ingredient and the inclusion material is about 1:7 to 1:20 in the composition.

In some embodiments, the molar ratio of the active ingredient to the inclusion material in the composition or formulation, or a mixture which is used to prepare the composition or formulation, is from about 1:0.5 to about 1:10. In some embodiments, the molar ratio is about 1:0.8 to about 1:10. In some embodiments, the molar ratio is about 1:1.4 to about 1:10. In some embodiments, the molar ratio is about 1:0.8 to about 1:2.5. In some embodiments, the molar ratio is about 1:1.4 to about 1:2.5.

In some embodiments, the inclusion material is selected from a group consisting of α-cyclodextrin, β-cyclodextrin, and γ-cyclodextrin and derivatives thereof. In some embodiments, the inclusion material is hydroxypropyl-β-cyclodextrin or sulfobutyl-β-cyclodextrin.

In some embodiments, the inclusion material is hydroxypropyl-β-cyclodextrin, the composition or formulation further comprises a stabilizing agent, and optionally comprises an acid reagent.

The stabilizing agent may comprise a water-soluble polymer or a surfactant. In some embodiments, the stabilizing agent is hypromellose.

In some embodiments, the acid reagent comprises at least one selected from a group consisting of an organic acid, a water-soluble acidic amino acid, a water-soluble inorganic acid and an acid salt. In some embodiments, the acid reagent comprises an organic acid. In some embodiments, the organic acid is citric acid and/or citric acid monohydrate.

In some embodiments, the composition or formulation comprises an active ingredient, an inclusion material and a stabilizing agent, optional an acid reagent; wherein the active ingredient is vilazodone or a pharmaceutically acceptable salt thereof, the inclusion material is hydroxypropyl-β-cyclodextrin, the stabilizing agent is hypromellose, and the acid reagent is citric acid and/or citric acid monohydrate.

In some embodiments, the composition or formulation is an oral formulation. In some embodiments, the composition or formulation is in the form of tablets, pills, capsules, granules, soft capsules, dry suspensions, or an oral liquid.

In some embodiments, the composition or formulation further comprises one or more pharmaceutically acceptable excipients.

In some embodiments, the pharmaceutically acceptable excipients comprise one or more of fillers, disintegrants, and lubricants. In some embodiments, the pharmaceutically acceptable excipients comprise one or more intragranular excipient(s) and one or more extragranular excipient(s).

In some embodiments, the filler is at least selected from lactose, sucrose, fructose, fructo-oligose, glucose, maltose, powdered sugar, D-mannitol, erythritol, xylitol, corn starch, potato starch, rice starch, part of the alpha starch, microcrystalline cellulose, calcium sulfate, calcium hydrogen phosphate and calcium carbonate; the disintegrant is at least selected from starch, microcrystalline cellulose, carboxymethylcellulose calcium, croscarmellose sodium, crospovidone, sodium carboxymethyl starch, low substituted hydroxypropylcellulose; and the lubricant is at least selected from magnesium stearate, calcium stearate, sodium stearyl fumarate, stearic acid, talc, polyethylene glycol, sucrose fatty acid esters, silicon dioxide, and a combination thereof.

In some embodiments, the formulation comprises about 2% w/w to about 8% w/w of vilazodone based on the total weight of the formulation. In some embodiments, the formulation comprises about 20% w/w to about 70% w/w of the inclusion material based on the total weight of the formulation. In some embodiments, the formulation comprises about 20% w/w to about 80% w/w of a filler based on the total weight of the formulation. In some embodiments, the formulation comprises about 0% w/w to about 25% w/w of a disintegrant based on the total weight of the formulation. In some embodiments, the formulation comprises about 0% w/w to about 2% w/w of a lubricant based on the total weight of the formulation. In some embodiments, the pharmaceutical formulation comprises about 2% to about 8% w/w of vilazodone. In some embodiments, the pharmaceutical formulation comprises about 30% to about 50% w/w of the inclusion material. In some embodiments, the pharmaceutical formulation comprises about 30% to about 50% w/w of the filler. In some embodiments, the pharmaceutical formulation comprises about 5% to about 15% w/w of the disintegrant. In some embodiments, the pharmaceutical formulation comprises about 0.5% to about 1.5% w/w of the lubricant.

In some embodiments, the pharmaceutical formulation comprises about 2% w/w to about 8% w/w of vilazodone, about 20% w/w to about 70% w/w of the inclusion material, about 20% w/w to about 80% w/w of the filler, about 0% w/w to about 25% w/w of the disintegrant, and about 0% w/w to about 2% w/w of the lubricant based on the total weight of the formulation. In some embodiments, the pharmaceutical formulation comprises about 2% w/w to about 8% w/w of vilazodone, about 30% w/w to about 50% w/w of the inclusion material, about 30% w/w to about 50% w/w of a filler, about 5% w/w to about 15% w/w of an disintegrant, and about 0.5% w/w to about 1.5% w/w of a lubricant based on the total weight of the formulation.

In some embodiments, the pharmaceutical formulation comprises about 5% w/w of vilazodone, about 40% w/w of the inclusion material, about 44% w/w of the filler, about 10% w/w of the disintegrant, and about 1% w/w of the lubricant based on the total weight of the formulation.

In another aspect, the present invention provides methods for preparing the inclusion complexes.

In some embodiments, a method for preparing the inclusion complexes comprises mixing the active ingredient and the inclusion material in a solvent to form an inclusion complex composition (e.g., an inclusion complex solution) containing the inclusion complex.

In some embodiments, a method for preparing the inclusion complexes comprises (1) preparing an inclusion complex solution; and (2) drying the inclusion complex solution to obtain a solid inclusion complex composition containing the inclusion complex.

In another aspect, also provided are methods of preparing the compositions or pharmaceutical formulations comprising the inclusion complex described herein.

In some embodiments, the method comprises mixing an inclusion complex composition comprising the inclusion complex with a pharmaceutically acceptable excipient.

In some embodiments, the method comprises: blending an inclusion complex composition comprising the inclusion complex with a pharmaceutically acceptable excipient, such as a filler, disintegrant, and/or lubricant to obtain total mixed particles; and compressing the total mixed particles into a pharmaceutical formulation, such as tablet cores.

In some embodiments, the method further comprises coating the tablet cores.

In some embodiments, the method comprises: a) dissolving the active ingredient and the inclusion material to form an inclusion complex solution; b) mixing the intragranular excipients and the inclusion complex solution, granulating and drying to form dry granules; and c) compressing the dry granules with extragranular excipients to form a pharmaceutical formulation, such as tablet cores.

In some embodiments, the method further comprises coating the tablet cores.

In some embodiments, the method comprises: a) dissolving the active ingredient and the inclusion material to form an inclusion complex solution; b) mixing the intragranular excipients such as the filler and the inclusion complex solution to obtain a mixture, granulating and drying the mixture in a fluidized bed granulator to obtain dry granules; and c) blending the dry granules with extragranular excipients to obtain the total mixed particles, pressing the total mixed particles to form a pharmaceutical formulation, such as tablet cores, or filling the total mixed particles in hard capsules.

In some embodiments, the method comprises: a) dissolving the active ingredient and the inclusion material to form an inclusion complex solution; and b) adding the filler to the inclusion complex solution, granulating and drying the resulted mixture to form dry granules.

In some embodiments, the method comprises mixing the active ingredient and the inclusion material in a solvent to obtain an inclusion complex or an inclusion complex composition (e.g., an inclusion complex solution or inclusion complex particles); then mixing the inclusion complex or the inclusion complex composition with a stabilizing agent and optional an acid reagent.

In some embodiments, the method comprises mixing the active ingredient and the inclusion material in a solvent to obtain an inclusion complex or an inclusion complex composition (e.g., an inclusion complex solution or inclusion complex particles); mixing the inclusion complex or the inclusion complex composition with a stabilizing agent and optional an acid reagent, then adding a pharmaceutically acceptable excipient. In some embodiments, the method comprises mixing the active ingredient and the inclusion material in a solvent to obtain an inclusion complex or an inclusion complex composition (e.g., an inclusion complex solution or inclusion complex particles); mixing the inclusion complex or the inclusion complex composition with a stabilizing agent, optional an acid reagent, and a pharmaceutically acceptable excipient; then forming a pharmaceutical formulation, such as tablets, pills, capsules, granules, soft capsules, dry suspensions or oral liquids, etc.

In some embodiments, the composition is a pharmaceutical formulation.

These and other aspects will be further described in the texts that follow.

DETAILED DESCRIPTIONS

As used in the present disclosure, the following words and phrases are generally intended to have the meanings as set forth below, except to the extent that the context in which they are used indicates otherwise.

The term "comprise" and variations thereof, such as, "comprises" and "comprising" are to be construed in an open, inclusive sense, that is, as "including, but not limited to." "Consisting essentially of" or its grammatic variants when used to define compositions and methods, shall mean excluding other elements of any essential significance to the compositions and methods for the intended use, but not excluding elements that do not materially affect the characteristic(s) of the compositions or methods. "Consisting of" or its grammatic variants shall mean excluding elements not specifically recited. Embodiments defined by each of these transition terms are within the scope of this invention. For example, when a formulation is described as comprising ingredients A, B and C, a formulation consisting essentially of A, B and C, and a formulation consisting of A, B and C are independently within the scope of this invention.

The term "optional" or "optionally" means that it may or may not be contained; for example: "optional an acid reagent" means that it may or may not contain an acid reagent.

The singular forms "a," "an," and "the" include plural references unless the context clearly dictates otherwise. For example, reference to "the excipient" includes a plurality of such excipients.

As used herein, the term "about" used in the context of quantitative measurements means the indicated amount ±10%, ±5%, or ±1% of the stated value. For example, "about 10" would mean 9-11, 9.5-10.5 or 9.9-10.1. The term "about X" also includes "X".

Recitation of numeric ranges of values throughout the disclosure is intended to serve as a shorthand notation of referring individually to each separate value falling within the range inclusive of the values defining the range, and each separate value is incorporated in the specification as it were individually recited herein.

The term "% w/w" as used herein refers to the weight of a component based on the total weight of a composition comprising the component. For example, if vilazodone is present in an amount of 50 mg in a composition having a total weight of 100 mg, then vilazodone is present in an amount of 50% w/w.

The term "pharmaceutically acceptable" refers to a material that is not biologically or otherwise undesirable, e.g., the material may be incorporated into a pharmaceutical formulation administered to a patient without causing any significant undesirable biological effects or interacting in a deleterious manner with any of the other components of the formulation in which it is contained. Pharmaceutically acceptable vehicles (e.g., carriers, adjuvants, and/or other excipients) have preferably met the required standards of toxicological and manufacturing testing and/or are included on the Inactive Ingredient Guide prepared by the U.S. Food and Drug Administration.

The term "excipient" or "pharmaceutically acceptable excipients" refers to fillers, diluents, disintegrants, precipitation inhibitors, surfactants, glidants, binders, lubricants, and other excipients and vehicles with which the compound is administered. Excipients are generally described herein and also in "Remington's Pharmaceutical Sciences" by E. W. Martin.

The term "filler" refers to chemical compounds that are added to an active ingredient facilitate formulation. Non-limiting examples of fillers include lactose, sucrose, fructose, fructo-oligose, glucose, maltose, powdered sugar and other sugars, D-mannitol, erythritol, xylitol and other sugar alcohols, corn starch, potato starch, rice starch, certain types of alpha starch and other starch, microcrystalline cellulose and other cellulose, calcium sulfate, calcium hydrogen phosphate and calcium carbonate and other inorganic salts.

The term "binder" when used herein relates to any pharmaceutically acceptable excipient which can be used to bind together the active ingredient and inert components together to maintain cohesive and discrete portions. Non-limiting examples of binders include hydroxypropylcellulose, hydroxypropylmethylcellulose, povidone, copovidone, and ethyl cellulose.

The term "disintegrant" refers to a substance which, upon addition to a solid preparation, facilitates its break-up or disintegration after administration and permits the release of an active ingredient. Non-limiting examples of disintegrants include starch, maize starch, sodium starch glycolate, cros- carmellose sodium, crospovidone, microcrystalline cellulose, modified corn starch, sodium carboxymethyl starch, povidone, pregelatinized starch, carboxymethylcellulose calcium, low substituted hydroxypropylcellulose, and alginic acid.

The term "lubricant" refers to a substance added to a powder blend to prevent the compacted powder mass from sticking to the equipment during the tableting or encapsulation process. A lubricant can aid the ejection of the tablet form the dies, and can improve powder flow. Non-limiting examples of lubricants include magnesium stearate, stearic acid, silica, fats, calcium stearate, polyethylene glycol, sodium stearyl fumarate, sucrose fatty acid esters, or talc; and solubilizers such as fatty acids including lauric acid, oleic acid, and $C_8/C_{10}$ fatty acid.

The term "coating" refers to a thin film on the surface of a substrate (e.g. tablet). Coatings can be useful in protecting the active ingredient(s) from photolytic degradation. Non-limiting examples of coatings include polyvinylalcohol based, hydroxyethylcellulose, hydroxypropylmethylcellulose, sodium carboxymethylcellulose, polyethylene glycol 4000 and cellulose acetate phthalate coatings.

As used herein, the term "reference listed drug" or "RLD" refers to the oral tablet approved by the U.S. FDA under NDA No. 022567 and marketed under the brand name VIIBRYD® which contains 10 mg, 20 mg or 40 mg of vilazodone hydrochloride in polymorph Form IV.

It would be understood that vilazodone refers to the compound, 5-(4-[4-(5-cyano-1H-indol-3-yl)butyl]-1-piperazinyl)-2-benzofuran-2-carboxamide, of the structure:

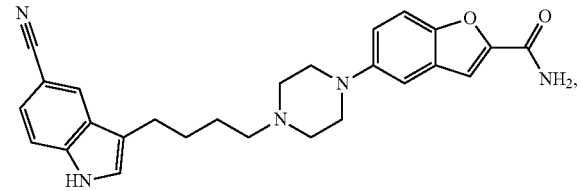 [SMILES: N#Cc1ccc2[nH]cc(CCCCN3CCN(c4ccc5oc(C(N)=O)cc5c4)CC3)c2c1]

or a pharmaceutically acceptable salt thereof. In some embodiments, vilazodone refers to 5-(4-[4-(5-cyano-1H-indol-3-yl)butyl]-1-piperazinyl)-2-benzofuran-2-carboxamide hydrochloride, i.e., vilazodone hydrochloride, or the hydrochloric acid salt of vilazodone. In some embodiments, the weight, weight ratio or weight percentage of vilazodone refers to the weight, weight ratio or weight percentage of vilazodone hydrochloride.

This disclosure provides solutions to at least the low bioavailability problem of vilazodone when administered in a fasted state, and allows vilazodone to be administered with or without food.

The label of current vilazodone drug product on the market, VIIBRYD® (the reference listed drug), indicates that it should be administered with food in order to achieve a 70% bioavailability and ensure effectiveness. Under fasted conditions, the bioavailability can be decreased by approximately 50%, which may result in diminished effectiveness in some patients.

The pharmaceutical formulations comprising vilazodone prepared using the microcarrier technology disclosed in CN104116741A exhibited a 50% dissolution rate of vilazodone in 0.1 N HCl after 60 minutes, which failed to produce a significant improvement in the dissolution rate over the reference listed drug VIIBRYD®, indicating that when the vilazodone formulations produced by the microcarrier technology are administered without food, the bioavailability of vilazodone still would not meet treatment requirement.

The inventors discovered that a main cause of the difference in vilazodone bioavailability between fasted and fed conditions is the significant difference in the solubility of vilazodone under different physiological pH conditions. Vilazodone is mainly absorbed in the small intestine where the physiological pH is about 6.8, and the solubility of vilazodone under such a pH is very low. Thus the amount and rate of vilazodone that is dissolved in the stomach will affect its absorption in the small intestine. Vilazodone dissolves well in a pH 3.1 buffer (simulated stomach fed conditions). Accordingly, when administered with food, vilazodone exhibits good release and bioavailability. However, in a 0.1 N HCl solution (simulated stomach fasted conditions), the solubility of vilazodone is poor, resulting in a significant reduction in bioavailability.

The inventors further discovered in one aspect, the inclusion complex of this technology comprising vilazodone exhibited good solubility, drug release and bioavailability in a pH 3.1 buffer (simulated stomach fed conditions), a 0.1 N HCl solution (simulated stomach fasted conditions), as well as a pH 6.8 buffer (simulated small intestine physiological conditions), thus reducing or eliminating the effect of pH on drug release. Further, the increase in vilazodone dissolution and bioavailability of the inclusion complex is not limited by the crystalline forms of vilazodone.

U.S. Pat. No. 8,673,921 (hereby incorporated by reference in its entirety) reports that vilazodone has a number of crystal polymorphs, among them Form IV has the best solubility and it is used in vilazodone formulations to ensure bioavailability. It was discovered that not only the dissolution rates of formulations prepared by the technology disclosed herein are unaffected by pH, the dissolution rates of the reported low solubility polymorphs are also significantly increased by this technology. As shown in the examples, using known formulation, the drug dissolution of Form XVI was lower than the reference listed drug comprising Form IV. However, using the technology disclosed herein, the dissolution of Form XVI was significantly increased. For example, even in a pH 6.8 media, the dissolution increased from single digit percentage to about 75% (Table 19 below).

Accordingly, provided herein is an oral formulation comprising vilazodone whose administration is not affected by food, thereby increasing patients' compliance and improve drug effectiveness.

In one aspect, provided herein is an inclusion complex comprising an active ingredient and an inclusion material. The active ingredient may be vilazodone or a pharmaceutically acceptable salt thereof. The inclusion material, for example, can be cyclodextrin or a derivative thereof or other molecules (e.g., inclusion compounds) capable of including the active ingredient. In some embodiments, one active ingredient molecule is included within the cavity of one inclusion material molecule. In some embodiments, one active ingredient molecule is included within the cavities of two inclusion material molecules.

Also provided are compositions and formulations comprising the inclusion complexes, and mixtures for preparing the inclusion complexes.

In some embodiments, based on weight ratio, at least about 50%, 55%, 60%, 65%, 70%, 75%, 80%, 85%, 90%, 95%, 98%, or 99% of the active ingredient is contained in inclusion complexes in the compositions or formulations.

In some embodiments, the weight ratio of the active ingredient to the inclusion material in the composition or formulation, or the mixture which is used to prepare the composition or formulation, is from about 1:2.4 to 1:45.4. In some embodiments, the weight ratio is 1:5 to 1:45.4. In some embodiments, the weight ratio is 1:6.5 to 1:45.4. In some embodiments, the weight ratio is 1:7 to 1:20. In some embodiments, the weight ratio is 1:6.5 to 1:11.5. In some embodiments, the weight ratio is 1:8 to 1:16.5. In some embodiments, the weight ratio is 1:8 to 1:10. In some embodiments, the weight ratio is 1:9.

According to some embodiments of the present invention, in some embodiments, the weight ratio of the active ingredient and the inclusion material hydroxypropyl-β-cyclodextrin is about 1:7 to 1:20 in the composition, which is beneficial to In some embodiments, in the composition, the weight ratio of the active ingredient to the inclusion material hydroxypropyl-β-cyclodextrin is about 1:7 to 1:15, which facilitates the dissolution of the active ingredient. In some embodiments, in the composition, the weight ratio of the active ingredient to the inclusion material hydroxypropyl-β-cyclodextrin is about 1:8 to 1:13, which is more conducive to the dissolution of the active ingredient. In some embodiments, in the composition, the weight ratio of the active ingredient to the inclusion material hydroxypropyl-β-cyclodextrin is about 1:8 to 1:10, which is more conducive to the dissolution of the active ingredient. In some embodiments, in the composition, the weight ratio of the active ingredient to the inclusion material hydroxypropyl-β-cyclodextrin is about 1:9, which is more conducive to the dissolution of the active ingredient.

In some embodiments, the molar ratio of the active ingredient to the inclusion material in the composition or formulation, or the mixture which is used to prepare the composition or formulation, is from 1:0.5 to 1:10. In some embodiments, the molar ratio is 1:0.8 to 1:10. In some embodiments, the molar ratio is 1:1.4 to 1:10. In some embodiments, the molar ratio is 1:0.8 to 1:2.5. In some embodiments, the molar ratio is 1:1.4 to 1:2.5.

In some embodiments, the active ingredient is vilazodone hydrochloride. In some embodiments, the active ingredient is a crystalline form of vilazodone. In some embodiments, the active ingredient is a crystalline form of vilazodone hydrochloride. In some embodiments, the active ingredient is an amorphous form of vilazodone and/or vilazodone hydrochloride. In some embodiments, the dissolution rate of a formulation comprising the inclusion complex in 0.1N HCl is as high as 90% or more, significantly higher than that of the reference listed drug. In some embodiments, the dissolution rate of a formulation comprising the inclusion complex is at least 10 times of the dissolution rate of the reference listed drug.

In some embodiments, the inclusion rate is at least 50%. In some embodiments, the inclusion rate is at least 80%. In some embodiments, the inclusion rate is at least 90%. In some embodiments, the inclusion rate is at least 95%. High inclusion rates lead to higher improvement in solubility and bioavailability under fasted conditions or the physiological conditions of the small intestine.

Cyclodextrin and its derivatives are compounds having sugar molecules (such as glucose) or derivatives thereof bound together in a ring (cyclic oligosaccharides). Derivatives of cyclodextrin including derivatives of α-cyclodextrin, β-cyclodextrin or γ-cyclodextrin in which the hydrogen atoms of one or more of the hydroxyl groups are replaced with a substituent, such as an alkyl or substituted alkyl (—R), acyl (—C(O)R), and sulfate (—S(O)$_2$OH or a salt thereof), wherein R is an alkyl or substituted alkyl. In some embodiments, R is an alkyl having 1, 2, 3, 4, 5, or 6 carbon atoms ($C_1$-$C_6$ alkyl), such as methyl, ethyl, propyl, isopropyl, butyl, isobutyl, pentyl, hexyl, etc. In some embodiments, R is an alkyl substituted with one or more substituents independently selected from hydroxy and sulfate, such as hydroxylmethyl (—$CH_2OH$), or sulfobutyl (—$CH_2CH_2CH_2CH_2S(O)_2OH$ or a salt thereof). Examples of cyclodextrin and its derivatives include but are not limited to α-cyclodextrin, β-cyclodextrin, γ-cyclodextrin, hydroxyethyl-β-cyclodextrin, hydroxypropyl-β-cyclodextrin (also known as hydroxypropyl betadex, beta cyclodextrin hydroxypropyl ethers or HPBCD), 2-hydroxypropyl)-β-cyclodextrin, sulfobutyl-β-cyclodextrin, dihydro-β-cyclodextrin, methyl-β-cyclodextrin, dimethyl-β-cyclodextrin, hydroxypropyl-γ-cyclodextrin, betadex sulfobutyl ether sodium (also known as sulfobutyl ether-beta-cyclodextrin, sulfobutyl ether-β-cyclodextrin sodium salt, sulfobutyl ether-β-cyclodextrin, sulfobutyl ether-β-cyclodextrin sodium salt, or SBE-β-CD or SBECD), glucose cyclodextrin, maltodextrin, carboxymethyl cyclodextrin, and sulfoalkyl cyclodextrin.

In some embodiments, the inclusion material is at least one selected from a group consisting of α-cyclodextrin, β-cyclodextrin and γ-cyclodextrin and derivatives thereof. In some embodiments, the inclusion material is hydroxypropyl-β-cyclodextrin or sulfobutyl-β-cyclodextrin.

In some embodiments, the inclusion material does not comprise lactose, mannitol, microcrystalline cellulose, or crospovidone.

In some embodiments, the composition comprising the inclusion complex is in a liquid form such as an inclusion complex solution or suspension. In some embodiments, the composition containing the inclusion complex is a solid inclusion complex composition.

The examples show that the technology disclosed herein allows vilazodone molecules enclosed inside the cavities of cyclodextrin or a derivative thereof. Upon inclusion, the crystalline form of the drug is lost and the drug enters the cavities of the inclusion material at a molecular level with high dispersion rate. It is surprisingly discovered that the solubility of the resulting inclusion complex is not significantly affected by pH, thereby improving bioavailability and ensuring the effectiveness of the drug when administered without food.

In another aspect, provided is a method for preparing the inclusion complex.

In some embodiments, the method comprises dissolving the active ingredient and the inclusion material in a solvent (such as an aqueous solvent, e.g., water) for a period of time, such as at least about 1 hour, at least about 2 hours, at least about 4 hours to form the inclusion complex.

In some embodiments, the method comprises: (1) preparing an inclusion complex solution; and (2) optionally drying the inclusion complex solution to obtain a solid inclusion complex composition comprising the inclusion complexes.

In some embodiments, the inclusion complex solution is prepared by mixing the active ingredient and the inclusion material in an aqueous solvent, such as water. In some embodiments, the inclusion complex solution is prepared by preparing a saturated aqueous solution. In some embodiments, the inclusion complex is prepared by grinding. In some embodiments, the active ingredient and the inclusion material are grinded in a sufficient amount of an aqueous solvent, such as water (e.g., at least about 5 mL, at least about 10 mL, at least about 20 mL per gram of the active ingredient) for a sufficient amount of time (e.g., at least about 1 hour, at least about 2 hours, at least about 4 hours) to form the inclusion complex. In some embodiments, the inclusion complex solution is prepared by an ultrasonic method. In some embodiments, a mixture of the active ingredient and the inclusion material in an aqueous solvent is treated with ultrasound until a solution is obtained.

In some embodiments, the method comprises elevating the temperature of the solvent to above room temperature and below the boiling point of the solvent, such as from about 40° C. to about 100° C., from about 60° C. to 90° C., or about 80° C.

In some embodiments, the solid inclusion complex composition is prepared by spray drying the inclusion complex solution. In some embodiments, the solid inclusion complex composition is prepared by freeze-drying the inclusion complex solution.

In some embodiments, the inclusion complex is prepared by a method comprising (1) preparing an inclusion complex solution by a method comprising at least one selected from a group consisting of preparing a saturated aqueous solution, grinding and ultrasonic methods; and (2) obtaining a solid inclusion complex composition comprising the inclusion complex by a method comprising spray-drying or freeze-drying the inclusion complex solution.

In another aspect, provided is a composition comprising the inclusion complex containing vilazodone or its pharmaceutically acceptable salt.

In another aspect, provided is a pharmaceutical formulation comprising the inclusion complex comprising vilazodone or its pharmaceutically acceptable salt.

In some embodiments, the composition or formulation is an oral formulation. In some embodiments, the composition or formulation is in the form of tablets, pills, capsules, granules, soft capsules, dry suspensions, or oral liquid.

In some embodiments, the composition or formulation further comprises one or more pharmaceutically acceptable excipients. In some embodiments, the pharmaceutically acceptable excipients include, but are not limited to one or more of fillers, disintegrants, and lubricants.

In some embodiments, the filler is selected from lactose, sucrose, fructose, fructo-oligose, glucose, maltose, powdered sugar, D-mannitol, erythritol, xylitol, corn starch, potato starch, rice starch, alpha starch, microcrystalline cellulose, calcium sulfate, calcium hydrogen phosphate and calcium carbonate, and a combination thereof. In some embodiments, the disintegrant is at least selected from starch, microcrystalline cellulose, carboxymethylcellulose calcium, croscarmellose sodium, crospovidone, sodium carboxymethyl starch, low substituted hydroxypropylcellulose, and a combination thereof. In some embodiments, the lubricant is at least selected from magnesium stearate, calcium stearate, sodium stearyl fumarate, stearic acid, talc, polyethylene glycol, sucrose fatty acid esters, silicon dioxide, and a combination thereof.

It was surprisingly found that the oral composition or formulation disclosed herein achieved high bioavailabilities when administered without food similar to administration with food, which reduces limitations on drug administration, increases patients' flexibility and compliance, as well as avoids possible ineffectiveness when improperly administered, thereby ensuring effectiveness. It is to be understood that the advantageous properties of the inclusion complex are found in the compositions or formulations comprising the inclusion complex.

The excipients in the compositions or formulations disclosed herein facilitate achievement of the effectiveness of the active ingredient in the inclusion complex, and allow convenient production, transportation, storage and administration. For example, addition of a filler improves molding, allowing easier administration; addition of a disintegrant facilitate rapid dissociation of the formulation and release of the active ingredient; and a lubricant reduces the stickiness of the drug during manufacture.

In some embodiments, the filler is one or more of lactose, sucrose, fructose, fructo-oligose, glucose, maltose, powdered sugar, D-mannitol, erythritol, xylitol, corn starch, potato starch, rice starch, alpha starch, microcrystalline cellulose, calcium sulfate, calcium hydrogen phosphate and calcium carbonate; the disintegrant is at least selected from starch, microcrystalline cellulose, carboxymethylcellulose calcium, croscarmellose sodium, crospovidone, sodium carboxymethyl starch, low substituted hydroxypropylcellulose; the lubricant is at least selected from magnesium stearate, calcium stearate, sodium stearyl fumarate, stearic acid, talc, polyethylene glycol, sucrose fatty acid esters, or silicon dioxide.

In some embodiments, the formulation comprises 2% w/w to 8% w/w of vilazodone based on the total weight of the formulation. In some embodiments, the formulation comprises 20% w/w to 70% w/w of a filler based on the total weight of the formulation. In some embodiments, the formulation comprises 0% w/w to 25% w/w of a disintegrant based on the total weight of the formulation. In some embodiments, the formulation comprises 0% w/w to 2% w/w of a lubricant based on the total weight of the formulation. In some embodiments, the pharmaceutical formulation comprises 2% to 8% w/w of vilazodone. In some embodiments, the pharmaceutical formulation comprises 30% to 50% w/w of the inclusion material. In some embodiments, the pharmaceutical formulation comprises 30% to 50% w/w of the filler. In some embodiments, the pharmaceutical formulation comprises 5% to 15% w/w of the disintegrant. In some embodiments, the pharmaceutical formulation comprises 0.5% to 1.5% w/w of the lubricant.

In some embodiments, the pharmaceutical formulation comprises 2% to 8% w/w of vilazodone, 20% to 70% w/w of the inclusion material, 20% to 80% w/w of the filler, about 0% to 25% w/w of the disintegrant, and 0% to 2% w/w of the lubricant, based on the total weight of the formulation. In some embodiments, the pharmaceutical formulation comprises 2% to 8% w/w of vilazodone, 30% to about 50% w/w of the inclusion material, 30% to 50% w/w of the filler, 5% to 15% w/w of the disintegrant, and 0.5% to 1.5% w/w of the lubricant, based on the total weight of the formulation.

In some embodiments, the pharmaceutical formulation comprises 5% w/w of vilazodone, 40% w/w of the inclusion material, 44% w/w of the filler, 10% w/w of the disintegrant, and 1% w/w of the lubricant, based on the total weight of the formulation.

In some embodiments, the pharmaceutically acceptable excipients comprise one or more intragranular excipient(s) (excipient(s) added before granulation and are part of the granules) and one or more extragranular excipient(s) (excipient(s) added to after granulation to be mixed with the granules).

In some embodiments, the inclusion material is hydroxypropyl-β-cyclodextrin. During the research process, the inventor found that the solubility of the inclusion complex prepared by using hydroxypropyl-β-cyclodextrin as the inclusion material was significantly improved, and the dissolution in different media (0.1N HCl and pH 6.8) was significantly higher than that of the reference listed drug VIIBRYD®. This suggests that the inclusion complex prepared with hydroxypropyl-β-cyclodextrin as the inclusion material can significantly improve the oral bioavailability of the active ingredient under fasting conditions. However, further studies have found that the dissolution of the active ingredient in the inclusion complex prepared by using hydroxypropyl-β-cyclodextrin as the inclusion material is not particularly stable in a pH 6.8 medium, and has a downward trend, especially under the condition of high strength (40 mg strength), the downward trend of the dissolution is more obvious. After research, the inventor found that increasing the weight ratio of hydroxypropyl-β-cyclodextrin to the active ingredient can reduce the tendency of the active ingredient in the composition or formulation to be unstable in the pH 6.8 medium, but it cannot completely solve the instability of the dissolution of the active ingredient in the pH 6.8 medium. The inventors respectively investigated the inclusion complexes or compositions of vilazodone hydrochloride and hydroxypropyl-β-cyclodextrin in weight ratio of 1:9, 1:13, 1:15 or 1:20, the results showed that increasing the proportion of hydroxypropyl-β-cyclodextrin in the inclusion complex can slow down the decline in the dissolution of the active ingredient in the pH 6.8 medium, but it cannot completely solve the problem of the decreased dissolution of the active ingredient. And when the proportion of hydroxypropyl-β-cyclodextrin increased to a certain degree, the degree of dissolution improvement did not increase significantly. Therefore, the inventors conducted further studies on the inclusion complexes using hydroxypropyl-β-cyclodextrin as the inclusion material and the compositions or formulations containing the inclusion complexes to develop a composition or formulation comprising the hydroxypropyl-β-cyclodextrin inclusion complex with a more stable dissolution of the active ingredient, to further improve the bioavailability of the active ingredient in the body after oral administration, so as to reduce the influence of food effects.

In order to further improve the dissolution stability of the active ingredient, further increase the bioavailability of the active ingredient in the body after oral administration, and reduce the influence of the food effects, through research, the inventors have found that a stabilizing agent can be added to the aforementioned compositions and/or formulations. In some embodiments, adding a stabilizing agent to the compositions and/or formulations is beneficial to slow down the downward tendency of the dissolution of the active ingredient.

Therefore, the present invention also provides a composition comprising the active ingredient, the inclusion material and a stabilizing agent, wherein the active ingredient is vilazodone or a pharmaceutically acceptable salt thereof.

Therefore, the present invention also provides a composition, which comprises the inclusion complex and a stabilizing agent, wherein the inclusion complex comprises the active ingredient and the inclusion material, and the active ingredient is vilazodone or a pharmaceutically acceptable salt thereof.

In some embodiments, the composition may comprise: the inclusion complex and a stabilizing agent, wherein the inclusion complex comprising the active ingredient contained in the inclusion material, the active ingredient is vilazodone or its pharmaceutically acceptable salt, and the inclusion material is hydroxypropyl-β-cyclodextrin. The stabilizing agent comprises a water-soluble polymer and/or a surfactant. The inventors found that when a water-soluble polymer is added to the inclusion complex, composition and/or formulation, the dissolution stability of the active ingredient in the inclusion complex, composition or formulation in a pH 6.8 medium can be significantly improved.

The water-soluble polymer comprises, but are not limited to: homopolymers or copolymers of N-vinyl lactams, such as polyvinylpyrrolidone (PVP), copolymer of polyvinylpyrrolidone and vinyl acetate, copolymer of polyvinylpyrrolidone and vinyl propionate, copolymer of N-vinylpyrrolidone and vinyl acetate, or copolymer of N-vinylpyrrolidone and vinyl propionate; polyacrylates or polymethacrylates, such as methacrylic acid-ethyl acrylate copolymer, methacrylic acid-methyl methacrylate copolymer, butyl methacrylate-methacrylic acid 2-dimethylaminoethyl copolymer, poly(hydroxyalkyl acrylate), poly(hydroxyalkyl methacrylate); polyacrylamides; vinyl acetate polymers, such as copolymer of vinyl acetate and crotonic acid, hydrogenated polyvinyl acetate (also called partially saponified polyvinyl alcohol); polyvinyl alcohol; oligosaccharides or polysaccharides, such as carrageenan, galactomannan, or xanthan gum; polymer polyethylene oxides, such as polyethylene oxide, polypropylene oxide, or copolymer of ethylene oxide and propylene oxide; cellulose ethers or cellulose esters, such as methyl cellulose, ethyl cellulose, hydroxyalkylcelluloses such as hydroxypropyl cellulose, hydroxyalkylalkylcelluloses such as hydroxypropyl methyl cellulose (HPMC), carboxymethyl cellulose sodium (CMC-Na), cellulose phthalates or cellulose succinates, such as cellulose acetate phthalate, hypromellose phthalate, hypromellose succinate or hypromellose acetate succinate.

According to some embodiments of the present invention, the water-soluble polymer preferably comprises at least one selected from a group consisting of N-vinylpyrrolidone based homopolymers and copolymers, methacrylic acid-based copolymers such as polyacrylic resin, polyethylene glycol-vinylcaprolactam-vinyl acetate copolymer, hydroxyalkylcelluloses such as hydroxypropylcellulose, hydroxyalkylalkylcelluloses such as hypromellose, cellulose phthalates such as hypromellose phthalate, and cellulose succinates such as hypromellose succinate or hypromellose acetate succinate; beneficial to improve the dissolution stability of the active ingredient in the pH 6.8 medium. In some embodiments, the water-soluble polymer preferably comprises at least one selected from a group consisting of polyvinylpyrrolidone (such as PVP K30), copovidone (such as VA64), hydroxypropylmethylcellulose (such as HPMC E5), carboxymethyl cellulose sodium (CMC-Na), hypromellose succinate and hypromellose acetate succinate, can improve the dissolution stability of the active ingredient in the pH 6.8 medium. In some embodiments, the water-soluble polymer preferably comprises at least one selected from a group consisting of hydroxypropyl methylcellulose (such as HPMC E5), polyvinylpyrrolidone (such as PVP K30), copovidone (such as VA64) and carboxymethyl cellulose sodium (CMC-Na), which can better improve the dissolution stability of the active ingredient in the pH 6.8 medium. In some embodiments, the water-soluble polymer is more preferably hypromellose, which can more significantly improve the dissolution stability of the active ingredient in the pH 6.8 medium.

The surfactant includes, but are not limited to: polyoxyethylene alkyl ethers, such as polyoxyethylene (3) lauryl ether, polyoxyethylene (5) cetyl ether, polyoxyethylene (2) stearyl ether, or polyoxyethylene oxyethylene (5) stearyl ether; polyoxyethylene alkyl aryl ethers, such as polyoxyethylene (2) nonyl phenyl ether, polyoxyethylene (3) nonyl phenyl ether, polyoxyethylene (4) nonyl phenyl ether, or polyoxyethylene (3) octyl phenyl ether; polyethylene glycol glycerides, such as PEG-200 monolaurate, PEG-200 dilaurate, PEG-300 dilaurate, PEG-400 dilaurate, PEG-300 distearate, PEG-300 dioleate; sucrose fatty acid esters, such as sucrose monostearate, sucrose distearate, sucrose monolaurate, or sucrose dilaurate; sorbitan fatty acid monoesters, such as sorbitan monolaurate, sorbitan monooleate, or sorbitan monopalmitate.

According to some embodiments of the present invention, the surfactant is preferably a surfactant with an HLB value (hydrophilic-lipophilic balance) not less than 6; it is beneficial to improve the dissolution stability of the active ingredient in the pH 6.8 medium.

According to some embodiments of the present invention, the surfactant is preferably at least one selected from a group consisting of Tween-80 (polyoxyethylene sorbitan monooleate), Span-20 (sorbitan fatty acid ester), polyoxyethylene castor oil, polyoxyethylene 40 hydrogenated castor oil (RH40), caprylic acid capric acid polyethylene glycol glyceride (Labrasol), polyethylene glycol hydroxystearate, polyethylene glycol glycerin laurate (Gelucire 44/14), poloxamer (polyoxyethylene polyoxypropylene ether block copolymer), (D)-α-tocopherol polyethylene glycol succinate and sodium lauryl sulfate, which is beneficial to improve the dissolution stability of the active ingredient in the pH 6.8 medium.

After research, the inventor found that the weight of the stabilizing agent can be 0.5%-10% of the total weight of the active ingredient, the inclusion material and the stabilizing agent, which has a stabilizing effect on the dissolution stability of the active ingredient. In some embodiments, the weight of the stabilizing agent may be 0.7%-7% of the total weight of the active ingredient, the inclusion material and the stabilizing agent, and has a good stabilizing effect on the dissolution stability of the active ingredient. In some embodiments, the weight of the stabilizing agent may be 0.99%-6.55% of the total weight of the active ingredient, the inclusion material and the stabilizing agent, and has a good stabilizing effect on the dissolution stability of the active ingredient.

In some embodiments, the weight of the stabilizing agent may be 0.1%-10% of the total weight of the composition or the formulation, and has a stabilizing effect on the dissolution stability of the active ingredient. In some embodiments, the weight of the stabilizing agent may be 0.5%-7% of the total weight of the composition or the formulation, and has a good stabilizing effect on the dissolution stability of the active ingredient. In some embodiments, the weight of the stabilizing agent may be 0.75%-5.5% of the total weight of the composition or the formulation, and has a good stabilizing effect on the dissolution stability of the active ingredient. In some embodiments, the weight of the stabilizing agent may be 1%-5%, or 1%-3% or 1%-2% of the total weight of the composition or the formulation, which is beneficial to the dissolution of the active ingredient and the preparation of the formulation.

According to some embodiments of the present invention, the stabilizing agent is hypromellose (HPMC), and its amount can be 0.5%-10% of the total weight of the active ingredient, the inclusion material and the stabilizing agent, and has a stabilizing effect on the dissolution stability of the active ingredient, preferably the amount is 0.7%-7%, and more preferably the amount is 0.99%-6.55%, which has a better stabilizing effect.

According to some embodiments of the present invention, the stabilizing agent is hypromellose, the weight of which can be 0.1%-10% of the total weight of the composition or the formulation, and has a stabilizing effect on the dissolution stability of the active ingredient. In some embodiments, the stabilizing agent is hypromellose, the weight of which can be 0.5%-7% of the total weight of the composition or the formulation, and has a good stabilizing effect on the dissolution stability of the active ingredient. In some embodiments, the stabilizing agent is hypromellose, the weight of which can be 0.75%-5.5% of the total weight of the composition or the formulation, and has a good stabilizing effect on the dissolution stability of the active ingredient. In some embodiments, the stabilizing agent is hypromellose, the weight of which is preferably 1%-5% of the total weight of the composition or the formulation, or 1%-4%, or 1%-3%, or 1%-2%, so that the active ingredient has better dissolution stability.

According to some embodiments of the present invention, in some embodiments, the composition comprises: the inclusion complex and the stabilizing agent, the inclusion complex comprising the active ingredient contained in the inclusion material; wherein the active ingredient is vilazodone or a pharmaceutically acceptable salt thereof, the inclusion material is hydroxypropyl-β-cyclodextrin, and the stabilizing agent is hypromellose.

According to some embodiments of the present invention, in some embodiments, the pharmaceutical formulation comprises: the aforementioned composition and one or more pharmaceutically acceptable excipients.

The inventors have discovered through research that the aforementioned compositions and/or formulations may comprise an acid reagent on the basis of containing the stabilizing agent, which can further increase the dissolution stability of the active ingredient in the pH 6.8 medium.

The acid reagent may comprise organic acids, water-soluble acidic amino acids, water-soluble inorganic acids or acid salts, and the like. The organic acids may comprise natural organic acids and synthetic organic acids, including but not limited to: carboxylic acids, sulfonic acids, sulfinic acids, and thiocarboxylic acids. The water-soluble acidic amino acid may comprise at least one selected from glutamic acid and aspartic acid. The acid salt may comprise at least one selected from acidic salts of glycine, alanine or serine, dihydrogen phosphate and hydrogen sulfate. In some embodiments, the acid reagent is an organic acid.

According to the embodiments of the present invention, in some embodiments, the organic acid preferably comprises at least one selected from a group consisting of citric acid, citric acid monohydrate, D-tartaric acid, L-tartaric acid, D-malic acid, L-malic acid, fumaric acid, maleic acid, succinic acid, oxalic acid and ascorbic acid, which is beneficial to improve the dissolution stability of the active ingredient in the pH 6.8 medium. According to the embodiments of the present invention, in some embodiments, the organic acid is more preferably citric acid and/or citric acid monohydrate, which can further improve the dissolution stability of the active ingredient in the pH 6.8 medium.

According to some embodiments of the present invention, based on weight ratio, when the ratio of the acid reagent in the composition or the formulation is 1%-10%, the dissolution of the active ingredient in the pH 6.8 medium is relatively stable, and the dissolution platform does not significantly decrease. According to some embodiments of the present invention, based on weight ratio, the ratio of the acid reagent in the composition or the formulation is preferably 1%-5%, more preferably 2%-4%, more preferably 3%, the dissolution of the active ingredient in the pH 6.8 medium is relatively stable, and the dissolution platform has not significantly decreased.

According to some embodiments of the present invention, in some embodiments, the composition comprises: the active ingredient, the inclusion material and the stabilizing agent, optionally an acid reagent; wherein the active ingredient is vilazodone or its pharmaceutically acceptable salt. In some embodiments, the composition comprises: the inclusion complex and the stabilizing agent, optionally an acid reagent, the inclusion complex comprises the active ingredient contained in the inclusion material; wherein, the active ingredient is vilazodone or a pharmaceutically acceptable salt thereof, and the inclusion material is hydroxypropyl-β-cyclodextrin. In some embodiments, the composition comprises: the inclusion complex and the stabilizing agent, optionally an acid reagent, the inclusion complex comprises the active ingredient contained in the inclusion material; wherein, the active ingredient is vilazodone or a pharmaceutically acceptable salt thereof, the inclusion material is hydroxypropyl-β-cyclodextrin, and the stabilizing agent is hypromellose. In some embodiments, the composition comprises: the inclusion complex and the stabilizing agent, optionally an acid reagent, and the inclusion complex comprises the active ingredient contained in the inclusion material; wherein, the active ingredient is vilazodone or a pharmaceutically acceptable salt thereof, the inclusion material is hydroxypropyl-β-cyclodextrin, the stabilizing agent is hypromellose, and the acid reagent is citric acid and/or citric acid monohydrate.

In some embodiments, the composition further comprises one or more pharmaceutically acceptable excipients.

According to some examples of the present invention, in some embodiments, the pharmaceutical formulation comprises: the active ingredient, the inclusion material, the stabilizing agent, and one or more pharmaceutically acceptable excipients, optionally comprising an acid reagent; wherein, the active ingredient is vilazodone or a pharmaceutically acceptable salt thereof. In some embodiments, the composition or pharmaceutical formulation comprises: the inclusion complex, the stabilizing agent, and one or more pharmaceutically acceptable excipients, optionally comprising an acid reagent; wherein, the inclusion complex comprises the active ingredient contained in the inclusion material, the active ingredient is vilazodone or a pharmaceutically acceptable salt thereof, the inclusion material is hydroxypropyl-β-cyclodextrin, the stabilizing agent is hypromellose, and the organic acid is citric acid and/or citric acid monohydrate.

In some embodiments, the aforementioned composition or pharmaceutical formulation provided herein comprises: the inclusion complex, the stabilizing agent, and one or more pharmaceutically acceptable excipients, optionally comprising an acid reagent; wherein the inclusion complex comprising the active ingredient contained in the inclusion material, the active ingredient is vilazodone or a pharmaceutically acceptable salt thereof, the inclusion material is hydroxypropyl-β-cyclodextrin, the stabilizing agent is hypromellose, and the acid reagent is citric acid and/or citric acid monohydrate; based on the total weight of the composition or formulation, the stabilizing agent is 0.1%-10% or 0.75%-7.5% of the composition or formulation, and the acid reagent is 1%-5% of the composition or formulation.

In some embodiments, the composition is a pharmaceutical formulation.

In some embodiments, in the composition or pharmaceutical formulation, based on weight ratio, at least 80%, 85% or 90% of the active ingredient is contained in the inclusion material or in the inclusion complex, which is conducive to the dissolution of the active ingredient. In some embodiments, in the composition or pharmaceutical formulation, based on weight ratio, at least 95% of the active ingredient is contained in the inclusion material or in the inclusion complex, which is more conducive to the dissolution of the active ingredient. In some embodiments, in the composition or pharmaceutical formulation, based on weight ratio, at least 99% of the active ingredient is contained in the inclusion material or in the inclusion complex, which is more conducive to the dissolution of the active ingredient.

The inclusion complexes, compositions and/or pharmaceutical formulations provided by the present invention can be used for patients in need to treat related diseases, such as depression and obsessive-compulsive disorder. The inclusion complexes, compositions and/or pharmaceutical formulations provided by the present invention can be taken with food, can be taken after eating, or taken on an empty stomach.

In another aspect, provided herein are methods of preparing the compositions or pharmaceutical formulations comprising the inclusion complex described herein.

In some embodiments, the method comprises mixing an inclusion complex composition comprising the inclusion complex with a pharmaceutically acceptable excipient.

In some embodiments, the method comprises: blending an inclusion complex composition comprising the inclusion complex with a pharmaceutically acceptable excipient, such as a filler, disintegrant, and/or lubricant to obtain total mixed particles; and compressing the total mixed particles into a pharmaceutical formulation, such as tablet cores.

In some embodiments, the method comprises: a) preparing a solid inclusion complex, which method comprises: weighing the inclusion material and the active ingredient, dissolving the inclusion material in water completely, adding the active ingredient while stirring, stirring the mixture in a water bath until a clear inclusion complex solution is obtained, and spray drying the mixture to obtain a solid inclusion complex composition comprising the inclusion complex; b) blending the inclusion complex composition with one or more of the filler, disintegrant, and lubricant to obtain total mixed particles; and c) compressing the total mixed particles to obtain tablet cores.

In some embodiments, the method comprises: a) dissolving the active ingredient and the inclusion material to form an inclusion complex solution; b) adding the intragranular excipients to the inclusion complex solution, granulating and drying the mixture to form dry granules; and c) compressing the dry granules with extragranular excipients to form tablet cores.

In some embodiments, the method comprises a) preparing an inclusion complex solution, which method comprises: weighing the inclusion material and the active ingredient, dissolving the inclusion material in water completely, adding the active ingredient while stirring, stirring the mixture in water bath until a clear inclusion complex solution is obtained; b) adding the intragranular excipients to the inclusion complex solution, granulating and drying the mixture in a fluidized bed granulator to obtain dry granules; and c) compressing the dry granules with extragranular excipients to obtain tablet cores.

In some embodiments, the method further comprises d) coating the tablet cores with a coating.

In some embodiments, the method comprises: a) preparing an inclusion complex solution, which method comprises: weighing the inclusion material and the active ingredient, dissolving the inclusion material in water completely, adding the active ingredient while stirring, stirring the mixture in water bath until a clear inclusion complex solution is obtained; b) adding the filler to the inclusion complex solution, granulating and drying the mixture in a fluidized bed granulator to obtain dry granules; and c) blending the dry granules with extragranular excipients to obtain the total mixed particles, pressing the total mixed particles, and filling the total mixed particles in hard capsules.

In some embodiments, the method comprises: a) preparing an inclusion complex solution, which method comprises: weighing the inclusion material and the active ingredient, dissolving the inclusion material in water completely, adding the active ingredient while stirring, stirring the mixture in water bath until a clear inclusion complex solution is obtained; and b) adding the filler to the inclusion complex solution, granulating and drying the mixture in a fluidized bed granulator to obtain dry granules.

According to some examples of the present invention, in some embodiments, the method for preparing the aforementioned compositions or pharmaceutical formulations comprises forming the inclusion complex.

In some embodiments, the method for preparing the aforementioned compositions or pharmaceutical formulations comprises: mixing vilazodone or a pharmaceutically acceptable salt thereof with hydroxypropyl-β-cyclodextrin to form the inclusion complex; then mixing the inclusion complex with the stabilizing agent and optional an acid reagent.

In some embodiments, the method for preparing the aforementioned compositions or pharmaceutical formulations comprises: mixing vilazodone or a pharmaceutically acceptable salt thereof with hydroxypropyl-β-cyclodextrin to form the inclusion complex; mixing the inclusion complex with the stabilizing agent, optional an acid reagent, and a pharmaceutically acceptable excipient; and then forming pharmaceutical formulations, such as tablets, pills, capsules, granules, soft capsules, dry suspensions or oral liquids, etc.

In some embodiments, the method for preparing the aforementioned compositions or pharmaceutical formulations comprises: mixing vilazodone or a pharmaceutically acceptable salt thereof, hydroxypropyl-β-cyclodextrin and water to form the inclusion complex; adding the stabilizing agent and optional an acid reagent and mixing well; adding a pharmaceutically acceptable excipient and mixing well, and then forming pharmaceutical formulations, such as tablets, pills, capsules, granules, soft capsules, dry suspensions or oral liquids, etc.

In some embodiments, the method for preparing the aforementioned compositions or pharmaceutical formulations comprises: mixing vilazodone or a pharmaceutically acceptable salt thereof with hydroxypropyl-β-cyclodextrin to form the inclusion complex; then mixing the inclusion complex with optional a pharmaceutically acceptable excipient and solidifying into particles; then adding the stabilizing and other pharmaceutically acceptable excipients, optionally an acid reagent; and then forming pharmaceutical formulations, such as tablets, pills, capsules, granules, soft capsules, dry suspensions or oral liquids, etc.

In some embodiments, inclusion complex is formed under heating, and the temperature of the heating is 60° C.-100° C., preferably is 80° C.-90° C.

In some embodiments, the method for preparing the aforementioned compositions or pharmaceutical formulations comprises:
1) mixing vilazodone or a pharmaceutically acceptable salt thereof with hydroxypropyl-β-cyclodextrin and water to form the inclusion complex under heating;
2) mixing the inclusion complex with a pharmaceutically acceptable excipient and solidifying into particles by a fluidized bed or spray drying;
3) mixing the particles with the stabilizing, other pharmaceutically acceptable excipients and optional an acid reagent, and forming pharmaceutical formulations, such as tablets, pills, capsules, granules, soft capsules, dry suspensions or oral liquids, etc.

In some embodiments, the method for preparing the aforementioned compositions or pharmaceutical formulations comprises: mixing vilazodone or a pharmaceutically acceptable salt thereof with hydroxypropyl-β-cyclodextrin to form the inclusion complex; mixing the inclusion complex with the stabilizing agent and optional an acid reagent, then mixing with optional a pharmaceutically acceptable excipient and solidifying into particles, then mixing with other pharmaceutically acceptable excipients and forming pharmaceutical formulations, such as tablets, pills, capsules, granules, soft capsules, dry suspensions or oral liquids, etc.

In some embodiments, the method for preparing the aforementioned compositions or pharmaceutical formulations comprises: mixing vilazodone or a pharmaceutically acceptable salt thereof with hydroxypropyl-β-cyclodextrin to form the inclusion complex; mixing the inclusion complex with the stabilizing agent, optionally an acid reagent; then mixing with a pharmaceutically acceptable excipient and solidifying into particles; then adding other pharmaceutically acceptable excipients, optional a stabilizing agent and optional an acid reagent and mixing well; then forming pharmaceutical preparations, such as tablets, pills, capsules, granules, soft capsules, dry suspensions or oral liquids, etc.

In some embodiments, the method for preparing the aforementioned compositions or pharmaceutical formulations comprises:
1) mixing vilazodone or its pharmaceutically acceptable salt, hydroxypropyl-β-cyclodextrin and water to form the inclusion complex under heating;
2) mixing the inclusion complex, the stabilizing and optional an acid reagent to obtain a mixture;
3) solidifying the mixture and optional a pharmaceutically acceptable excipient into particles by fluidized bed or spray drying;
4) optionally mixing the particles and other pharmaceutically acceptable excipients, and forming pharmaceutical formulations.

In some embodiments, the method for preparing the aforementioned compositions or pharmaceutical formulations comprises:
1) mixing vilazodone or its pharmaceutically acceptable salt, hydroxypropyl-β-cyclodextrin and water to form the inclusion complex under heating;
2) mixing the inclusion complex, hypromellose and optional an organic acid to obtain a mixture;
3) solidifying the mixture and optional a pharmaceutically acceptable excipient into particles by a fluidized bed or spray drying;
4) optionally mixing the particles with other pharmaceutically acceptable excipients, and forming pharmaceutical formulations.

In some embodiments, the method for preparing the aforementioned compositions or pharmaceutical formulations comprises:
1) mixing vilazodone or its pharmaceutically acceptable salt, hydroxypropyl-β-cyclodextrin and water to form the inclusion complex under heating;
2) mixing the inclusion complex, hypromellose and optional an organic acid to obtain a mixture;
3) solidifying the mixture and optional a pharmaceutically acceptable excipient into particles by a fluidized bed or spray drying;
4) mixing the particles with other pharmaceutically acceptable excipients, optional a stabilizing agent and optional an acid reagent, and forming pharmaceutical formulations.

In the above methods, the temperature of heating may be from 60° C. to 100° C., preferably is from 80° C. to 90° C.

In some embodiments, the method for preparing the aforementioned compositions or pharmaceutical formulations preferably comprises forming the inclusion complex first, and then mixing the inclusion complex with the stabilizing agent and optional an acid reagent to obtain a mixture; then mixing the mixture with optional a pharmaceutically acceptable excipient and solidifying into particles; and then optionally mixing the particles with other pharmaceutically acceptable excipients, and forming pharmaceutical formulations. This method is more smooth and convenient in operation, and makes the mixing of various materials more uniform, the drug dispersibility is better, and it is more conducive to obtaining a composition with better dissolution.

In some embodiments, the method for preparing the aforementioned compositions or pharmaceutical formulations comprises tabletting and coating to form a pharmaceutical formulation. In some embodiments, the method comprises filling a capsule to prepare a pharmaceutical formulation. In some embodiments, the method comprises preparing the composition into granules or dry suspensions.

In some embodiments, the aforementioned compositions are pharmaceutical formulations.

In the aforementioned methods, in the prepared inclusion complexes, based on weight ratio, at least 50%, 55%, 60%, 65%, 70%, 75%, 80%, 85%, 90%, 95% or 99% of the active ingredient is contained in the inclusion material, which is conducive to the dissolution of the composition. In some embodiments, in the aforementioned methods, in the prepared inclusion complexes, based on weight ratio, at least 90% of the active ingredient is contained in the inclusion material, which is more conducive to the dissolution of the composition. In some embodiments, in the aforementioned methods, in the prepared inclusion complexes, based on weight ratio, at least 95% of the active ingredient is contained in the inclusion material, which is more conducive to the dissolution of the composition. In some embodiments, in the aforementioned methods, in the prepared inclusion complexes, based on weight ratio, at least 99% of the active ingredient is contained in the inclusion material, which is more conducive to the dissolution of the composition.

The above methods can prepare the provided compositions or pharmaceutical formulations containing the aforementioned inclusion complex. The compositions or pharmaceutical formulations have a stable dissolution in the pH 6.8 medium without a significant drop in the dissolution platform, have better dissolution stability, and can obtain good oral bioavailability, and significantly improve the bioavailability administered orally under fasting conditions.

BRIEF DESCRIPTION OF THE DRAWINGS

FIG. 1 is an average plasma concentration-time curve of the composition detected in example 19.

EXAMPLES

It will be understood by those skilled in the art that the following examples are intended to be illustrative of the invention and are not to be construed as limiting the disclosure. Persons skilled in the art may modify, adjust, substitute or vary the examples. Unless specifically stated otherwise, specific techniques or conditions that are not expressly described in the following examples may be ascertained by conventional techniques or conditions in the art or in accordance with the product specifications. The drugs, reagents or instruments used without specific indications of the manufacturer are commercially available products.

Among them, the reference listed drug VIIBRYD® used in the examples was 10 mg vilazodone hydrochloride tablet which was prepared by Merck KGaA Germany.

Unless specifically stated, the following testing methods were used in the following examples:

HPLC: Agilent 1260;

Chromatographic conditions: UV 242 nm detection wavelength, chromatographic column:kromasil 100-5 C18 4.6 mm*150 mm, 5 microns, mobile phase: 0.02 M pH 6.0 potassium hydrogen phosphate and acetonitrile at 54:46 (V/V), flow rate: 1.0 mL/minute, injection volume: 10 microliters, runtime: 4.5 minutes.

Comparative Example 1

In Comparative Example 1, vilazodone was micronized without addition of cyclodextrin. The micronized vilazodone was mixed with lactose, microcrystalline cellulose, silicon dioxide and magnesium stearate according to Table 1 to form total mixed granules, which were compressed into 100.0 mg vilazodone tablets (C1).

TABLE 1

Ingredients of Comparative Example Tablets C1

| Ingredient | Weight (g) |
|---|---|
| Vilazodone hydrochloride (From IV) | 5.00 |
| Lactose | 25.00 |
| Microcrystalline cellulose | 18.50 |
| Silicon dioxide | 1.00 |
| Magnesium stearate | 0.50 |

Vilazodone tablets C1 were put in a 0.1% acetic acid dissolution medium having a pH of 3.1 which is in vitro simulation of fed conditions, a 0.1 N HCl dissolution medium simulating fasted conditions, and a dissolution medium having a pH of 6.8 simulating the intestinal conditions. Drug dissolution was detected by a dissolution apparatus using the US Pharmacopoeia paddle method (USP II) at a speed of 60 RPM. An aliquot of the solution of each time point was taken, and filtered with a 0.45 micron microporous membrane. The filtrate of each sample was analyzed by HPLC. The results are shown in Tables 11-13.

Comparative Example 2

In Comparative Example 2, vilazodone hydrochloride was mixed with lactose monohydrate, and β-cyclodextrin in Table 2, and the mixture was milled to a particle size of about 20 μm, mixed with other excipients in Table 2, and compressed into vilazodone tablets having a total weight of 100.0 mg (C2). The tablets were subjected to in vitro dissolution test according to the method described in Comparative Example 1. The results are shown in Tables 11-13.

TABLE 2

Ingredients of Comparative Example Tablets C2

| Ingredient | Weight (%, w/w) |
|---|---|
| Vilazodone hydrochloride (From IV) | 10.00 |
| Lactose monohydrate | 25.00 |
| β-Cyclodextrin | 25.00 |
| Microcrystalline cellulose | 29.00 |
| Sodium carboxymethyl starch | 5.00 |
| Silicon dioxide | 3.00 |
| Magnesium stearate | 3.00 |
| Total | 100.00 |

Comparative Example 3

In Comparative Example 3, vilazodone hydrochloride was mixed with hydroxypropyl-β-cyclodextrin, and the mixture was milled to a particle size of about 5 μm. The particles were dispersed in an aqueous solution of polysorbate 80, dried and blended evenly with other excipients in Table 3, and directly compressed into tablets (C3). The tablets were subjected to in vitro dissolution test according to the method described in Comparative Example 1. The results are shown in Tables 11-13.

TABLE 3

Ingredients of Comparative Example Tablets C3

| Ingredient | Weight (%, w/w) |
|---|---|
| Vilazodone hydrochloride (From IV) | 10.00 |
| Hydroxypropyl-β-cyclodextrin | 10.00 |
| Starch | 29.95 |
| Lactose monohydrate | 40.00 |
| Sodium carboxymethylcellulose | 5.00 |
| Sodium lauryl sulfate | 3.00 |
| Polysorbate 80 | 0.05 |
| Silicon dioxide | 1.00 |
| Magnesium stearate | 1.00 |
| Total | 100.00 |

Example 1

In Example 1, vilazodone hydrochloride (API) and beta-dex sulfobutyl ether sodium (SBE-β-CD) in ratios according to Table 4 were stirred in water at 80° C. in a water bath for 4 hours, to form inclusion complex solutions, which were lyophilized to obtain inclusion complex compositions as powders.

TABLE 4

Ratios of Vilazodone Hydrochloride and Betadex Sulfobutyl Ether Sodium

| | Molar Ratio | | Weight Ratio | | Water |
|---|---|---|---|---|---|
| No. | API (mol) | SBE-β-CD (mol) | API (g) | SBE-β-CD (g) | (g) |
| 0 | 1.0 | 0.2 | 1.0 | 1.0 | 1.387 |
| 1 | 1.0 | 0.5 | 1.0 | 2.4 | 3.329 |
| 2 | 1.0 | 0.8 | 1.0 | 3.5 | 4.855 |
| 3 | 1.0 | 1.4 | 1.0 | 6.5 | 9.016 |
| 4 | 1.0 | 2.5 | 1.0 | 11.4 | 15.812 |
| 5 | 1.0 | 10.0 | 1.0 | 45.4 | 62.970 |

A sample of each inclusion complex solution was filtered through a 0.45 micron filter membrane and the subsequent filtrate was subjected to HPLC testing to determine the content of the dmg in the inclusion complex solution. Inclusion rate=included dmg amount/total dmg amount× 100%. The results are shown in Table 5.

TABLE 5

Inclusion Amounts and Rates

| No. | Volume (mL) | Total API amount (g) | API Inclusion Amount (g) | Inclusion Rate (%) | API: SBE-β-CD Weight Ratio (%) |
|---|---|---|---|---|---|
| 1-0 | 25.0 | 8.626 | 1.811 | 21.0 | 1:1 |
| 1-1 | 25.0 | 3.620 | 1.245 | 34.4 | 1:2.4 |
| 1-2 | 25.0 | 2.475 | 1.175 | 47.5 | 1:3.5 |
| 1-3 | 25.0 | 1.142 | 1.062 | 93.0 | 1:6.5 |
| 1-4 | 25.0 | 0.762 | 0.709 | 93.0 | 1:11.4 |
| 1-5 | 25.0 | 0.190 | 0.187 | 98.4 | 1:45.4 |

Vilazodone inclusion complexes 1-0 to 1-5, C1, and reference listed drug (RLD) (10 mg each) were subjected to in vitro dissolution tests in a 0.1 N HCl and a pH 6.8 buffer according to the method described in Comparative Example 1. The results are shown in Tables 6-7.

TABLE 6

Cumulative Dissolution Rate in 0.1N HCl

| No. | 10 min (%) | 15 min (%) | 20 min (%) | 30 min (%) | 45 min (%) |
|---|---|---|---|---|---|
| 0 | 31 ± 1.15 | 34 ± 0.58 | 38 ± 1.00 | 44 ± 1.00 | 48 ± 1.15 |
| 1 | 47.0 ± 1.0 | 53.0 ± 3.5 | 59.0 ± 0.6 | 64.0 ± 1.0 | 67.0 ± 1.2 |
| 2 | 56.0 ± 3.6 | 61.0 ± 2.3 | 66.0 ± 2.1 | 71.0 ± 2.3 | 74.0 ± 3.0 |
| 3 | 76.0 ± 2.5 | 81.0 ± 1.5 | 81.0 ± 2.5 | 81.0 ± 1.0 | 79.0 ± 2.6 |
| 4 | 90.0 ± 2.0 | 96.0 ± 1.5 | 98.0 ± 0.0 | 98.0 ± 0.6 | 98.0 ± 0.6 |
| 5 | 96.0 ± 2.5 | 102.0 ± 0.6 | 100.0 ± 0.6 | 102.0 ± 0.6 | 101.0 ± 0.6 |
| C1 | 14.0 ± 3.1 | 21.0 ± 1.0 | 24.0 ± 1.2 | 30.0 ± 1.0 | 35.0 ± 0.6 |
| RLD | 25.0 ± 2.9 | 33.0 ± 2.1 | 38.0 ± 1.2 | 46.0 ± 4.2 | 56.0 ± 1.5 |

TABLE 7

Cumulative Dissolution Rate in pH 6.8 Buffer

| No. | 10 min (%) | 15 min (%) | 20 min (%) | 30 min (%) | 45 min (%) |
|---|---|---|---|---|---|
| 0 | 20 ± 1.15 | 23 ± 0.58 | 24 ± 1.00 | 23 ± 0.00 | 22 ± 0.58 |
| 1 | 31 ± 2 | 38 ± 5 | 47 ± 1.7 | 54 ± 3.5 | 58 ± 3 |
| 2 | 36 ± 2.5 | 45 ± 4 | 48 ± 3.6 | 50 ± 6.7 | 56 ± 2.9 |
| 3 | 65 ± 1 | 75 ± 2.5 | 76 ± 3.8 | 66 ± 3.2 | 77 ± 4.4 |
| 4 | 81 ± 4.5 | 93 ± 1 | 94 ± 1 | 95 ± 1.2 | 95 ± 0.6 |
| 5 | 89 ± 2.1 | 94 ± 3.5 | 98 ± 1 | 98 ± 1.5 | 98 ± 2.1 |
| C1 | 0 ± 0 | 0 ± 0 | 0 ± 0 | 1 ± 0 | 1 ± 0 |
| RLD | 2 ± 0.6 | 4 ± 0.6 | 4 ± 0.6 | 5 ± 0 | 6 ± 0.6 |

Results

When the weight ratio of vilazodone hydrochloride to SBE-β-CD is 1:1 (1-0), the dissolution of the API in 0.1 N HCl was low and the bioavailability was not significantly improved. In comparison, when the weight ratio of vilazodone hydrochloride to SBE-β-CD was 1:2.4 to 45.4 (1-1 to 1-5), and the inclusion rate of vilazodone hydrochloride increased from 34.4% to 98.4%. When the weight ratio of vilazodone hydrochloride to SBE-β-CD was 1:45.4, the inclusion rate reached about 100% (1-5). Further increases in the amount of SBE-β-CD did not increase the cumulative release of the drug, but would increase the production cost as more SBE-β-CD would be used.

In summary, when the weight ratio of vilazodone hydrochloride to SBE-β-CD was 1:2.4 to 1:45.4, the inclusion and dissolution rates as well as the production costs were optimized. The solubility of the drug was improved significantly under simulated fasted conditions. Considering production cost and solubility, the effect was better when the weight ratio of vilazodone hydrochloride to SBE-β-CD is 1:6.5 to 1:11.5. The test results show that encapsulating vilazodone hydrochloride in the cavity of the inclusion material could result in a good solubility at 0.1 N HCl and pH 6.8, leading to complete release of the drug.

Example 2

In Example 2, vilazodone hydrochloride and α-cyclodextrin according to Table 8 were added to purified water with stirring. The mixture was stirred at 80° C. for 4 hours to form a clear inclusion complex solution. The inclusion complex solution was spray dried to form vilazodone hydrochloride inclusion complex composition as a solid powder. The vilazodone hydrochloride inclusion complex composition was mixed with microcrystalline cellulose, lactose, crospovidone and magnesium stearate according to Table 8 to obtain blended granules, which were compressed into tablets having a total weight of 381.2 mg (A1).

TABLE 8

Ingredients of Tablets A1 Comprising Inclusion Complex

| Ingredient | Weight (g) |
|---|---|
| Vilazodone hydrochloride (From IV) | 0.65 |
| α-cyclodextrin | 10.50 |
| Purified water | 31.34 |
| Microcrystalline Cellulose | 6.63 |
| Lactose | 2.57 |
| Crospovidone | 2.29 |
| Magnesium stearate | 0.23 |

In Example 2, the dissolution rate of vilazodone hydrochloride inclusion complex tablets was accessed in a pH 3.1 dissolution medium (0.1% acetic acid), a 0.1 N HCl dissolution medium and a pH 6.8 dissolution medium according to the test conditions of Comparative Example 1. After the in vitro dissolution test, the test solution was filtered through a 0.45 micron microfiltration membrane and the filtrate was subjected to HPLC analysis. The results are shown in Tables 11-13.

Example 3

In Example 3, the tablet formulation (A2) shown in Table 9 comprising vilazodone inclusion complex having a total tablet weight of 200.0 mg/tablet was prepared and tested as described in Example 2. The results are shown in Tables 11-13.

TABLE 9

Ingredients of Tablets A2 Comprising Inclusion Complex

| Ingredient | Weight (g) |
|---|---|
| Vilazodone hydrochloride (From IV) | 5.00 |
| γ-cyclodextrin | 40.00 |
| Purified water | 40.00 |
| Microcrystalline cellulose | 29.00 |
| Lactose | 15.00 |
| Crospovidone | 10.00 |
| Magnesium stearate | 1.00 |

Example 4

In Example 4, the vilazodone tablets (A3) were prepared as described in Example 3 with the exception that γ-cyclodextrin was replaced with hydroxypropyl-β-cyclodextrin. The in vitro dissolution of the tablets A3 was tested as described in Example 2 and the results are shown in Tables 11-13.

Example 5

In Example 5, the specific formulation of the vilazodone tablet (A4) was shown in Table 10. Vilazodone hydrochloride and betadex sulfobutyl ether sodium were added to purified water at 80° C. with stirring, and the mixture was stirred for 4 hours to form a clear solution. The inclusion complex solution was used as the granulating solution, microcrystalline cellulose and croscarmellose sodium were used as the substrate in a subsequent granulating process to form granules. The granules were dried by fluid bed to form dry granules. The dry granules were mixed with extragranular excipients crospovidone and magnesium stearate to form blended granules, and the blended granules were compressed to form vilazodone tablets weighing 216.2 mg each. The drug dissolution of the vilazodone inclusion complex tablets A4 was assessed in dissolution mediums having pH 3.1 (0.1% acetic acid), 0.1 N HCl or pH 6.8. After in vitro dissolution test, the test solution was filtered through a 0.45 micron microfiltration membrane and the filtrate was analyzed by HPLC. The results are shown in Tables 11-13.

TABLE 10

Ingredients of Tablets A4 Comprising Inclusion Complex

| Ingredient | Weight (g) |
|---|---|
| Vilazodone hydrochloride (From IV) | 40.00 |
| Sulfobutyl-β-cyclodextrin | 320.00 |
| Purified water | 400.00 |
| Microcrystalline cellulose (intragranular) | 300.00 |
| Croscarmellose sodium (intragranular) | 100.00 |
| Crospovidone (extragranular) | 100.00 |
| Magnesium stearate (extragranular) | 4.80 |

Results

Tables 11-13 show the results of the dissolution test of the formulations A1-A4 of Examples 2-5, Comparative Examples C1-C3, and RLD in dissolution mediums having a pH of 3.1 (0.1% acetic acid), 0.1 N HCl or a pH of 6.8, respectively.

TABLE 11

Cumulative Dissolution at pH 3.1

| Formulation | 10 min (%) | 15 min (%) | 20 min (%) | 30 min (%) | 45 min (%) |
|---|---|---|---|---|---|
| A1 | 56.0 ± 1.5 | 79.0 ± 3.2 | 99.0 ± 4.6 | 104.0 ± 0.6 | 104.0 ± 1.0 |
| A2 | 89.0 ± 3.1 | 92.0 ± 1.0 | 94.0 ± 1.5 | 93.0 ± 1.0 | 91.0 ± 4.2 |
| A3 | 83.0 ± 6.6 | 95.0 ± 1.7 | 94.0 ± 1.5 | 95.0 ± 2.1 | 95.0 ± 3.5 |
| A4 | 69.0 ± 12.1 | 95.0 ± 4.4 | 101.0 ± 3.4 | 102.0 ± 1.3 | 101.0 ± 3 |
| C1 | 68.0 ± 11.0 | 82.0 ± 5.6 | 89.0 ± 2.0 | 91.0 ± 1.5 | 92.0 ± 3.6 |
| C2 | 97 ± 1.00 | 97 ± 1.00 | 97 ± 1.53 | 97 ± 2.00 | 97 ± 1.53 |
| C3 | 56 ± 1.73 | 63 ± 0.58 | 67 ± 0.58 | 75 ± 1.00 | 81 ± 1.53 |
| RLD | 87.0 ± 2.3 | 93.0 ± 1.0 | 93.0 ± 1.0 | 93.0 ± 1.7 | 93.0 ± 0.6 |

TABLE 12

Cumulative Dissolution in 0.1N HCl

| Formulation | 10 min (%) | 15 min (%) | 20 min (%) | 30 min (%) | 45 min (%) |
|---|---|---|---|---|---|
| A1 | 39.0 ± 2.3 | 60.0 ± 2.5 | 76.0 ± 1.5 | 95.0 ± 0.0 | 97.0 ± 0.0 |
| A2 | 88.0 ± 0.0 | 93.0 ± 0.6 | 92.0 ± 1.0 | 93.0 ± 0.6 | 93.0 ± 1.0 |
| A3 | 92.0 ± 1.5 | 97.0 ± 0.6 | 99.0 ± 1.0 | 98.0 ± 1.0 | 98.0 ± 2.1 |
| A4 | 71.0 ± 9.7 | 97.0 ± 7.2 | 99.0 ± 2.3 | 100.0 ± 1.8 | 100.0 ± 1.6 |
| C1 | 14.0 ± 3.1 | 21.0 ± 1.0 | 24.0 ± 1.2 | 30.0 ± 1.0 | 35.0 ± 0.6 |
| C2 | 51 ± 1.00 | 53 ± 2.52 | 57 ± 0.58 | 61 ± 0.00 | 64 ± 0.00 |
| C3 | 55 ± 1.15 | 43 ± 2.00 | 36 ± 3.06 | 28 ± 2.00 | 19 ± 1.00 |
| RLD | 25.0 ± 2.9 | 33.0 ± 2.1 | 38.0 ± 1.2 | 46.0 ± 4.2 | 56.0 ± 1.5 |

TABLE 13

Cumulative Dissolution at pH 6.8

| Formulation | 10 min (%) | 15 min (%) | 20 min (%) | 30 min (%) | 45 min (%) |
|---|---|---|---|---|---|
| A1 | 26 ± 3.5 | 48 ± 11.1 | 69 ± 25.6 | 75 ± 9 | 77 ± 3.8 |
| A2 | 54 ± 3.5 | 70 ± 7.5 | 76 ± 5.3 | 77 ± 1 | 74 ± 5.1 |
| A3 | 69 ± 10.7 | 81 ± 3.6 | 86 ± 3.2 | 88 ± 2.5 | 83 ± 3.5 |
| A4 | 70 ± 2.6 | 80 ± 1.5 | 81 ± 1.5 | 82 ± 3.5 | 82 ± 3.1 |
| C1 | 0 ± 0 | 0 ± 0 | 0 ± 0 | 1 ± 0 | 1 ± 0 |
| C2 | 13 ± 0.58 | 15 ± 0.58 | 16 ± 0.58 | 16 ± 0.58 | 16 ± 0.00 |
| C3 | 15 ± 8.72 | 23 ± 2.31 | 24 ± 3.00 | 26 ± 1.53 | 26 ± 1.00 |
| RLD | 2 ± 0.6 | 4 ± 0.6 | 4 ± 0.6 | 5 ± 0 | 6 ± 0.6 |

As shown in Tables 11-13, the dissolution rates of A1-A4 were similar to C1-C3 and RLD at pH 3.1 (0.1% acetic acid) with cumulative dissolution rates of more than 93% at 45 min. The cumulative release of C1 (micronized) and RLD in 0.1 N HCl was only 35% and 56% at 45 min, respectively. The cumulative release of C2-C3, which are formulations prepared in accordance with CN104116741A, was 64% and 19%, respectively. By comparison, the cumulative release of A1-A4 reached 93% to 100% at 45 min, with the cumulative dissolution rate at each time point being significantly higher than that of C1 and RLD. The results show that the dissolution improvement of the formulations A1-A4 disclosed herein over C2-C3 was more prominent at 0.1 N HCl. At pH 6.8, the cumulative release rates of A1-A4 at 45 min were about 3 times or higher of the mere 1%-26% of C1-C3 and 6% of RLD.

Example 6

The specific formulation of vilazodone formulation of Example 6 is shown in Table 14. Vilazodone and sulfobutyl-β-cyclodextrin were added to purified water at 80° C. with stirring, and the mixture was stirred for 4 hours to form a clear inclusion complex solution. The inclusion complex solution was used as the granulating solution, and microcrystalline cellulose as the substrate in the subsequent granulating process to form granules, which were dried by a fluid bed granulator to form dry vilazodone granules. The dry granules were mixed with extragranular excipient magnesium stearate to form total mixed granules, which were compressed to tablets each comprising 40 mg vilazodone hydrochloride. Alternatively, the total mixed granules were filled into hard capsules to form capsules. Dissolution of the vilazodone tablets was determined in dissolution mediums having 0.1 N HCl, pH 3.1 or pH 6.8, respectively, using the procedure described in Example 2. The results are shown in Table 15. As the results show, the dissolution of the vilazodone tablets in 0.1 N HCl, pH 3.1 and pH 6.8 mediums are similar and not affected by the pH value, reaching to nearly 100% in 15 minutes.

TABLE 14

Ingredients of Formulation of Example 6 Comprising Inclusion Complex

| Ingredient | Weight (g) |
|---|---|
| Vilazodone hydrochloride (From IV) | 100.00 |
| SBE-β-CD | 900.00 |
| Purified water | 900.00 |
| Microcrystalline cellulose | 300.00 |
| Magnesium stearate (extragranular) | 10.00 |

TABLE 15

Cumulative Dissolution of Tablets of Example 6

| Dissolution Medium | 5 min (%) | 10 min (%) | 15 min (%) | 20 min (%) | 30 min (%) | 45 min(%) |
|---|---|---|---|---|---|---|
| 0.1N HCl | 53 ± 2.12 | 87 ± 1.41 | 98 ± 0.00 | 98 ± 0.00 | 98 ± 0.00 | 98 ± 0.00 |
| pH 3.1 | 52 ± 2.00 | 85 ± 0.58 | 97 ± 0.58 | 98 ± 0.00 | 98 ± 0.58 | 98 ± 0.00 |
| pH 6.8 | 46 ± 0.58 | 78 ± 1.00 | 93 ± 0.00 | 95 ± 0.00 | 95 ± 0.58 | 95 ± 0.58 |

Example 7

The specific formulation of Example 7 is shown in Table 16. Vilazodone and sulfobutyl-β-cyclodextrin were added to purified water at 80° C. with stirring and the mixture was stirred for 4 hours to form a clear inclusion complex solution. The inclusion complex solution was used as a granulating solution, and sucrose as the substrate in the subsequent granulation process to form granules which were dried by a fluid bed granulator to form dry vilazodone granules.

TABLE 16

Ingredients of Formulation of Example 7 Comprising Inclusion Complex

| Ingredient | Weight (g) |
|---|---|
| Vilazodone hydrochloride (From IV) | 100.00 |
| SBE-β-CD | 900.00 |
| Purified water | 900.00 |
| Sucrose | 3200.00 |

Example 8

The specific formulation of Example 8 is shown in Table 17. Vilazodone (Crystalline From XVI) and sulfobutyl-β-cyclodextrin were added to purified water at 80° C. with stirring, and the mixture was stirred for 4 hours to form a clear inclusion complex solution. The inclusion complex solution was used as the granulating solution, and microcrystalline cellulose and lactose as the substrate in the subsequent granulation process and the resulting granules were dried by a fluid bed granulator to form dry vilazodone granules. The dry vilazodone granules were mixed with extragranular excipients to form total mixed granules, and the total mixed granules were compressed to form tablets. Vilazodone tablets were subjected to dissolution tests in dissolution mediums having 0.1 N HCl, a pH of 3.1 or a pH of 6.8 respectively under conditions as describe in Example 2. The in vitro dissolution test results are shown in Table 19.

TABLE 17

Ingredients of Formulation of Example 8 Comprising Inclusion Complex

| Ingredient | Weight (g) |
|---|---|
| Vilazodone hydrochloride (From XVI) | 53.90 |
| SBE-β-CD | 511.50 |
| Microcrystalline cellulose | 312.29 |
| Lactose | 80.74 |
| Vilazodone hydrochloride (From X VI) (extragranular) | 23.10 |
| Crospovidone (extragranular) | 107.69 |
| Sodium stearyl fumarate (extragranular) | 10.78 |

Comparative Example 4

In Comparative Example 4, vilazodone (Form XVI) was micronized without addition of cyclodextrin. The micronized vilazodone was mixed with lactose, microcrystalline cellulose, silicon dioxide and magnesium stearate according to Table 18 to form total mixed granules. The total mixed granules were compressed into 100.0 mg vilazodone tablets (C4). The vilazodone tablets were subjected to dissolution tests in dissolution mediums having 0.1 N HCl, a pH of 3.1 or a pH of 6.8 respectively under test conditions as described in Example 2. The in vitro dissolution test results are shown in Table 19.

TABLE 18

Ingredients of Formulation of Comparative Example 4

| Ingredient | Weight (g) |
|---|---|
| Vilazodone hydrochloride (From XVI) | 5.00 |
| Lactose | 25.00 |
| Microcrystalline cellulose | 18.50 |
| Silicon dioxide | 1.00 |
| Magnesium stearate | 0.50 |

TABLE 19

Cumulative Dissolution Percentage Comparison of Tablets of Example 8, Comparative Example 4 and RLD

| Dissolution medium | Exp. | 10 min | 15 min | 20 min | 30 min | 45 min |
|---|---|---|---|---|---|---|
| pH 3.1 | Exp. 8 | 85 ± 9.07 | 96 ± 2.00 | 98 ± 1.53 | 98 ± 2.08 | 99 ± 2.08 |
|  | C4 | 63 ± 4.7 | 73 ± 2.1 | 79 ± 1.7 | 85 ± 2.1 | 88 ± 2.9 |
|  | RLD | 87 ± 2.30 | 93 ± 1.00 | 93 ± 1.00 | 93 ± 1.70 | 93 ± 0.60 |
| 0.1N HCl | Exp. 8 | 81 ± 0.58 | 90 ± 1.73 | 91 ± 2.08 | 95 ± 0.58 | 97 ± 0.00 |
|  | C4 | 11 ± 0.6 | 15 ± 0.6 | 19 ± 0.6 | 22 ± 0.6 | 27 ± 1.2 |
|  | RLD | 25 ± 2.90 | 33 ± 2.10 | 38 ± 1.20 | 46 ± 4.20 | 56 ± 1.50 |
| pH 6.8 | Exp. 8 | 70 ± 0.58 | 73 ± 0.58 | 74 ± 1.15 | 74 ± 0.58 | 75 ± 0.58 |
|  | C4 | 0 ± 0 | 0 ± 0 | 0 ± 0 | 1 ± 0.6 | 1 ± 0 |
|  | RLD | 2 ± 0.60 | 4 ± 0.60 | 4 ± 0.60 | 5 ± 0 | 6 ± 0.60 |

In Example 8, Form XVI of vilazodone hydrochloride reported in U.S. Pat. No. 8,673,921 was used. As shown by the results of C4 and RLD in Table 19, the crystalline forms of vilazodone also have an effect on the dissolution. Using the inclusion technology, vilazodone exhibited good solubility and a higher bioavailability regardless of the crystalline forms.

Example 9

Six beagle dogs were randomly divided into two groups in double crossover experiments under fasted and fed conditions. The dogs were given orally A4 (10 mg tablet) or C1. Whole blood samples were taken at 0.25, 0.5, 1, 2, 4, 6, 8, 10, 24 hours. Plasma samples were prepared as follows: whole blood 200-400 μL was placed in a centrifuge tube, $K_2EDTA$ was added as an anticoagulant, and centrifuged for 60 min. The plasma samples were kept at −70° C. The concentration of vilazodone in the blood plasma was measured by a validated LC-MS/MS method and pharmacokinetic parameters were assessed with non-compartment model using WinNonlin 6.3 software. The results are shown in Table 20.

TABLE 20

Pharmacokinetics Parameters in Fasted and Fed Dogs

| Pharmacokinetic parameters (n = 3) | | $T_{max}$ (h) | $C_{max}$ (ng/ml) | $AUC_{last}$ (h*ng/ml) |
|---|---|---|---|---|
| A4, fasted | Mean | 0.9 | 116 | 398 |
|  | CV % | 22 | 45 | 71 |
| A4, fed | Mean | 1.8 | 90.1 | 341.4 |
|  | CV % | 58 | 66 | 77 |
| C1, fasted | Mean | 1.0 | 25.4 | 105.2 |
|  | CV % | 0 | 57 | 55 |
| C1, fed | Mean | 1.7 | 67.8 | 293.8 |
|  | CV % | 31 | 48 | 86 |

As shown in Table 20, the plasma concentration-time curve ($AUC_{last}$) and the peak plasma concentration ($C_{max}$) of A4 (tablets prepared in example 5) under fasted conditions were higher than under fed conditions, achieving the purpose of improving the bioavailability under fasted conditions. By comparison, the $C_{max}$ of C1 under fasted conditions was only about 37.5% of the $C_{max}$ under fed conditions and the $AUC_{last}$ of C1 under fasted conditions was only about 35.8% of the $AUC_{last}$ under fed conditions.

Example 10

Six Beagle dogs were randomly divided into two groups in double crossover experiments under fasted and fed conditions, respectively. The dogs were given orally A4 (10 mg tablet) or RLD (10 mg). Whole blood samples of the dogs were analyzed according to the procedure described in Example 9 and the results are shown in Table 21.

TABLE 21

Pharmacokinetics Parameters in Fasted and Fed Dogs

| Pharmacokinetic parameter (n = 3) | | $T_{max}$ (h) | $C_{max}$ (ng/mL) | $AUC_{last}$ (h*ng/mL) |
|---|---|---|---|---|
| A4, fasted | Mean | 0.8 | 148.7 | 451.7 |
|  | CV % | 31.0 | 41.6 | 54.0 |
| A4, fed | Mean | 1.0 | 106.2 | 343.3 |
|  | CV % | 54.8 | 30.8 | 37.5 |
| RLD, fasted | Mean | 1.5 | 24.6 | 109.3 |
|  | CV % | 36.5 | 77.1 | 85.6 |
| RLD, fed | Mean | 2.3 | 76.7 | 267.2 |
|  | CV % | 79.8 | 74.1 | 70.4 |

As shown in Table 21, the $AUC_{last}$ and $C_{max}$ of A4 under fasted conditions were higher than the $AUC_{last}$ and $C_{max}$ under fed conditions, achieving the purpose of improving the bioavailability under fasted conditions. By comparison, the $C_{max}$ of RLD under fasted conditions was only about 32.1% of the $C_{max}$ of RLD under fed conditions, and the $AUC_{last}$ of RLD under fasted conditions was about 41% of the $AUC_{last}$ of RLD under fed conditions.

Example 11

According to the inclusion technology disclosed herein, 10 mg vilazodone coated tablets comprising the inclusion complex were prepared according to the formulation of Example 8, and given to three Beagle dogs orally under fasted or fed conditions in a double crossover experiment.

Whole blood samples were collected and analyzed as described in Experiment 9. The results are shown in Table 22.

TABLE 22

Pharmacokinetics Parameters in Fasted and Fed Dogs

| Pharmacokinetic parameters (n = 3) | | $T_{max}$ (h) | $C_{max}$ (ng/mL) | $AUC_{last}$ (h*ng/ml) |
|---|---|---|---|---|
| fasted | Mean | 0.67 | 111.04 | 382.91 |
|  | CV % | 43.3 | 43.1 | 54.0 |
| fed | Mean | 2.0 | 96.52 | 382.64 |
|  | CV % | 86.5 | 63.43 | 59.6 |

As shown in Table 22, $AUC_{last}$ and $C_{max}$ of the coated tablets were similar under fasted and fed conditions, achieving bioequivalence under fasted and fed conditions.

As shown in Experiments 9-11, the formulations comprising the vilazodone inclusion complex exhibited improved absorption of vilazodone when taken with or without food, which reduces variability in therapeutic effect due to food effect, and ensures drug performance and improves patients' flexibility and compliance. In addition, vilazodone inclusion complex and formulations comprising the complex can be prepared conveniently with low production cost and under industrial manufactural conditions.

Example 12

According to the formulations in Table 23, the prescribed amount of hydroxypropyl-β-cyclodextrin (HP-(3-CD) was added to purified water, stirred to dissolve; then vilazodone hydrochloride (API) was added, heated to 85° C., stirred until the solution was clear to obtain an inclusion complex solution. According to the dissolution method in Comparative Example 1, the dissolution of 40 mg strength inclusion complex solution samples in a pH 6.8 medium was measured respectively. The specific results are shown in Table 24.

TABLE 23

Formulations of inclusion complexes with different amounts of HP-β-CD (unit: g)

| Component | Formulation 1 | Formulation 2 | Formulation 3 | Formulation 4 | Formulation 5 | Formulation 6 |
|---|---|---|---|---|---|---|
| Vilazodone hydrochloride | 40.00 | 40.00 | 40.00 | 40.00 | 40.00 | 40.00 |
| HP-β-CD | 360.00 | 520.00 | 600.00 | 800.00 | 280.00 | 320.00 |
| Purified Water [1] | 360.00 | 520.00 | 600.00 | 800.00 | 280.00 | 320.00 |

TABLE 24

Dissolution data of inclusion complex samples with different ratios of HP-β-CD in pH 6.8 media

|  | 5 min | 10 min | 15 min | 20 min | 30 min | HP-β-CD: API (w/w) |
|---|---|---|---|---|---|---|
| Formulation 1 | 79 ± 1.41 | 83 ± 2.83 | 80 ± 1.41 | 79 ± 1.41 | 68 ± 13.44 | 9:1 |
| Formulation 2 | 88 ± 0.71 | 91 ± 3.54 | 93 ± 4.95 | 91 ± 2.12 | 85 ± 4.24 | 13:1 |
| Formulation 3 | 85 ± 1.41 | 89 ± 0.71 | 96 ± 7.78 | 88 ± 2.12 | 82 ± 2.12 | 15:1 |
| Formulation 4 | 93 ± 3.54 | 96 ± 2.83 | 95 ± 1.41 | 94 ± 0.00 | 84 ± 2.12 | 20:1 |
| Formulation 5 | 84 ± 2.65 | 86 ± 4.51 | 81 ± 11.24 | 65 ± 20.95 | 35 ± 22.01 | 7:1 |
| Formulation 6 | 91 ± 2.83 | 93 ± 1.41 | 95 ± 4.24 | 94 ± 0.71 | 86 ± 1.41 | 8:1 |

The above results show that when the weight ratio of HP-β-CD to API is greater than 7:1, the dissolution of the prepared inclusion complex is significantly higher than that of the RLD, indicating that, the solubility of vilazodone hydrochloride was significantly improved after being prepared into an inclusion complex. As the dissolution rate of vilazodone hydrochloride has been significantly improved, its dissolution in the pH 6.8 medium has also appeared unstable, and the dissolution platform has decreased. But by increasing the amount of hydroxypropyl-β-cyclodextrin, the dissolution stability of the prepared inclusion complex solution in a pH 6.8 medium has been improved to a certain extent, with a downward trend slowed down. When the weight ratio of HP-β-CD to API is greater than 13:1, further increasing the amount of HP-β-CD will not significantly increase the dissolution stability.

Example 13

According to the formulations in Table 25, the prescribed amount of hydroxypropyl-β-cyclodextrin was added to purified water and stirred to dissolve; then vilazodone hydrochloride was added, heated to 85° C., stirred until the solution was clear to obtain an inclusion complex solution; then water-soluble polymers were added, stirred and dissolved to obtain a mixture of vilazodone hydrochloride. According to the dissolution method in Comparative Example 1, the dissolution of 40 mg strength samples in pH 6.8 medium was measured. The specific results are shown in Table 26.

talline cellulose in a fluidized bed granulator and granulated to obtain dry granules; then the water-soluble polymer and sodium stearyl fumarate were added, mixed evenly and compressed into tablets. According to the dissolution method in Comparative Example 1, the dissolution of 40 mg strength tablet samples in 0.1N HCl and a pH 6.8 medium was measured respectively. The specific results are shown in Table 28.

TABLE 25

Formulations of samples with different water-soluble polymers (unit: g)

| Component | Formulation 1 | Formulation 7 | Formulation 8 | Formulation 9 | Formulation 10 | Formulation 11 |
|---|---|---|---|---|---|---|
| Vilazodone hydrochloride | 40.00 | 40.00 | 40.00 | 40.00 | 40.00 | 40.00 |
| HP-β-CD | 360.00 | 280.00 | 320.00 | 360.00 | 360.00 | 360.00 |
| Purified Water [1] | 360.00 | 280.00 | 320.00 | 360.00 | 360.00 | 360.00 |
| Hypromellose E5 | — | 4.20 | 4.80 | 15.20 | — | — |
| Povidone K30 | — | — | — | — | 15.20 | — |
| Carboxymethyl cellulose sodium | — | — | — | — | — | 15.20 |

TABLE 26

Dissolution data of samples with different water-soluble polymers in pH 6.8 media

| | 5 min | 10 min | 15 min | 20 min | 30 min | 45 min |
|---|---|---|---|---|---|---|
| Formulation 1 | 79 ± 1.41 | 83 ± 2.83 | 80 ± 1.41 | 79 ± 1.41 | 68 ± 13.44 | — |
| Formulation 7 | 85 ± 5.69 | 90 ± 5.86 | 90 ± 6.11 | 90 ± 3.21 | 95 ± 4.04 | 89 ± 4.73 |
| Formulation 8 | 87 ± 7.23 | 91 ± 7.00 | 90 ± 12.12 | 93 ± 9.02 | 94 ± 8.50 | 94 ± 6.11 |
| Formulation 9 | 88 ± 2.12 | 88 ± 2.12 | 85 ± 1.41 | 87 ± 5.66 | 85 ± 1.41 | 84 ± 0.71 |
| Formulation 10 | 83 ± 0.71 | 88 ± 0.71 | 89 ± 1.41 | 89 ± 4.24 | 87 ± 2.12 | 86 ± 0.71 |
| Formulation 11 | 83 ± 0.71 | 86 ± 0.71 | 86 ± 0.71 | 84 ± 0.71 | 87 ± 0.71 | 87 ± 6.36 |

The data of example 12 and example 13 shows that when the stabilizing agent water-soluble polymer is combined with the inclusion complex, the dissolution stability of the prepared composition in the pH 6.8 medium is significantly improved. Compared with formulation 1, after adding the stabilizing agent water-soluble polymer, the dissolution platform of the prepared composition at 45 minutes did not significantly decrease. When the weight ratio of HP-β-CD to API is 7:1 to 9:1 and after adding 1.30% to 3.66% (w/w, excluding water) of stabilizing agent to the composition, the dissolution platform of the prepared composition has been improved in the pH 6.8 medium.

Example 14

According to the formulations in Table 27, the prescribed amount of hydroxypropyl-β-cyclodextrin, was added to purified water, stirred to dissolve, then vilazodone hydrochloride was added, heated to 85° C., stirred until the solution was clear to obtain an inclusion complex solution. The inclusion complex solution was sprayed on microcrys-

TABLE 27

Formulations of tablets with different water-soluble polymers (unit: g)

| Component | Formulation 12 | Formulation 13 | Formulation 14 | Formulation 15 |
|---|---|---|---|---|
| Vilazodone hydrochloride | 40.00 | 40.00 | 40.00 | 40.00 |
| HP-β-CD | 360.00 | 360.00 | 360.00 | 360.00 |
| Purified Water [1] | 360.00 | 360.00 | 360.00 | 360.00 |
| Microcrystalline cellulose | 109.00 | 109.00 | 109.00 | 109.00 |
| Colloidal silicon dioxide | 3.00 | 3.00 | 3.00 | 3.00 |
| Hypromellose E5 | — | 30.00 | — | — |
| Carboxymethyl cellulose sodium (CMC-Na) | — | — | 4.00 | — |
| Copovidone | — | — | — | 30.00 |
| Sodium stearyl fumarate | 8.00 | 4.00 | 4.00 | 4.00 |
| Total | 520 | 546 | 520 | 546 |

Remarks: The purified water in 1 is removed during fluidized bed granulation and drying.

TABLE 28

Dissolution data of tablets with different water-soluble polymers

| Medium | Formulation | 5 min | 10 min | 15 min | 20 min | 30 min | 45 min |
|---|---|---|---|---|---|---|---|
| 0.1N HCl | Formulation 12 | 36 ± 5.29 | 53 ± 0.58 | 73 ± 0.58 | 89 ± 0.58 | 100 ± 1.00 | 101 ± 0.00 |
|  | Formulation 13 | 24 ± 0.00 | 46 ± 0.00 | 64 ± 0.58 | 81 ± 1.53 | 99 ± 2.00 | 102 ± 0.00 |
|  | Formulation 14 | 31 ± 0.58 | 57 ± 1.00 | 77 ± 1.00 | 92 ± 0.00 | 101 ± 0.58 | 102 ± 0.58 |
|  | Formulation 15 | 25 ± 1.00 | 47 ± 0.58 | 65 ± 0.58 | 82 ± 0.58 | 101 ± 1.00 | 104 ± 0.58 |
| pH 6.8 | Formulation 12 | 28 ± 1.00 | 50 ± 1.15 | 61 ± 1.73 | 44 ± 12.66 | 11 ± 3.79 | 5 ± 0.58 |
|  | Formulation 13 | 22 ± 0.58 | 43 ± 1.53 | 58 ± 3.61 | 70 ± 1.00 | 82 ± 1.15 | 83 ± 1.53 |
|  | Formulation 14 | 24 ± 0.58 | 46 ± 0.58 | 61 ± 1.00 | 69 ± 1.53 | 76 ± 0.58 | 75 ± 2.31 |
|  | Formulation 15 | 23 ± 0.58 | 43 ± 1.73 | 58 ± 1.00 | 70 ± 1.15 | 79 ± 1.00 | 79 ± 1.15 |

The above data shows that after the hydroxypropyl-β-cyclodextrin inclusion complex solution of vilazodone hydrochloride is granulated and compressed, the dissolution stability of the active ingredient in the pH 6.8 medium was reduced. The dissolution stability of the prepared plain tablets in the pH 6.8 medium is lower than that of the inclusion complex solutions; however, after adding 0.77%-5.49% (w/w) of the water-soluble polymer to the formulation, the dissolution stability of the prepared plain tablets in the pH 6.8 medium has been significantly improved, and the dissolution platform at 45 minutes did not appear to be significantly reduced. According to the mass concentration meter (w/v, g/ml), when the water-soluble polymer in the tablets is completely dissolved in the dissolution medium, its concentration is about 0.4%-3.0% (w/v, g/ml), it shows that as long as there is a small amount of stabilizing agent in the composition, the dissolution stability of vilazodone can be greatly improved.

Example 15

According to the formulations in Table 29, the dry granules were prepared according to the process of Example 14, and then the prescribed amounts of hypromellose, organic acid and sodium stearyl fumarate were added, mixed evenly, and compressed into tablets. According to the dissolution method in Comparative Example 1, the dissolution of 40 mg strength tablet samples in pH 6.8 medium was measured, and the pH value of the medium at the end of dissolution was tested. The specific results are shown in Table 30.

TABLE 29

Formulations of tablets with different organic acids (unit: g)

| Component | Formulation 16 | Formulation 17 | Formulation 18 | Formulation 19 | Formulation 20 |
|---|---|---|---|---|---|
| Vilazodone hydrochloride | 40.00 | 40.00 | 40.00 | 40.00 | 40.00 |
| HP-β-CD | 400.00 | 400.00 | 400.00 | 400.00 | 400.00 |
| Purified Water [1] | 400.00 | 400.00 | 400.00 | 400.00 | 400.00 |
| Microcrystalline cellulose | 104.50 | 104.50 | 104.50 | 104.50 | 104.50 |
| Colloidal silicon dioxide | 2.75 | 2.75 | 2.75 | 2.75 | 2.75 |
| Hypromellose E5 | 5.75 | 5.75 | 5.75 | 5.75 | 5.75 |
| Citric acid monohydrate | — | 19.50 | — | — | — |
| Fumaric acid | — | — | 19.50 | — | — |
| Succinic acid | — | — | — | 19.50 | — |
| L-tartaric acid | — | — | — | — | 19.50 |
| Sodium Stearyl Fumarate | 2.50 | 2.50 | 2.50 | 2.50 | 2.50 |
| Total | 555.5 | 575 | 575 | 575 | 575 |

Remarks: The purified water in 1 is removed during fluidized bed granulation and drying.

TABLE 30

Dissolution data of tablet samples with different organic acids

|  | 5 min | 10 min | 15 min | 20 min | 30 min | 45 min | 60 min | 90 min |
|---|---|---|---|---|---|---|---|---|
| Formulation 16 pH = 6.80 | 32 ± 2.83 | 58 ± 1.41 | 75 ± 0.71 | 83 ± 1.41 | 82 ± 8.49 | 84 ± 0.00 | 79 ± 0.00 | 74 ± 0.71 |
| Formulation 17 pH = 6.81 | 34 ± 0.58 | 61 ± 1.73 | 79 ± 1.00 | 86 ± 1.53 | 87 ± 1.00 | 89 ± 2.52 | 86 ± 2.08 | 87 ± 2.08 |
| Formulation 18 pH = 6.78 | 32 ± 1.00 | 58 ± 1.00 | 75 ± 1.73 | 83 ± 2.52 | 84 ± 2.31 | 84 ± 0.58 | 84 ± 0.58 | 85 ± 5.03 |
| Formulation 19 pH = 6.82 | 34 ± 1.15 | 60 ± 1.73 | 77 ± 2.31 | 85 ± 2.52 | 85 ± 0.71 | 85 ± 1.41 | 87 ± 2.12 | 87 ± 0.75 |
| Formulation 20 pH = 6.78 | 32 ± 1.53 | 59 ± 0.00 | 77 ± 2.00 | 85 ± 2.08 | 84 ± 2.08 | 84 ± 1.53 | 81 ± 0.58 | 82 ± 0.71 |

The above data shows that adding an organic acid in the case that a water-soluble polymer is already contained in the formulation can further increase the dissolution stability of the active ingredient in the pH 6.8 medium. The dissolution platform of the prepared plain tablets did not significantly decrease at 90 minutes. By measuring the pH value of the medium at the end of the dissolution, it was found that the addition of a small amount of organic acid did not significantly change the pH value of the medium system, indicating that the addition of the organic acid did not increase the dissolution stability of the tablets by changing the pH value of the medium (it is speculated that the possible reason is that the inclusion complex forms a more stable triple complex with water-soluble polymers and organic acids, which ultimately leads to a more stable dissolution platform of vilazodone hydrochloride in a pH 6.8 medium). The results of this experiment suggest that the composition containing a stabilizing agent and an organic acid has higher oral bioavailability in vivo.

Example 16

According to the formulations in Table 31, the dry granules were prepared according to the process of Example 14, and then the prescribed amounts of hypromellose, citric acid monohydrate and sodium stearyl fumarate were added, mixed evenly, and compressed into tablets. According to the dissolution method in Comparative Example 1, the dissolution of 40 mg strength samples in pH 6.8 medium was measured, and the pH value of the dissolution medium at the end of the dissolution was detected. The specific results are shown in Table 32.

TABLE 31

Formulations of tablets with different amounts of citric acid monohydrate (unit: g)

| Component | Formulation 21 | Formulation 22 | Formulation 23 | Formulation 24 | Formulation 25 |
|---|---|---|---|---|---|
| Vilazodone hydrochloride | 40.00 | 40.00 | 40.00 | 40.00 | 40.00 |
| HP-β-CD | 400.00 | 400.00 | 400.00 | 400.00 | 400.00 |
| Purified Water [1] | 400.00 | 400.00 | 400.00 | 400.00 | 400.00 |
| Microcrystalline cellulose | 104.50 | 104.50 | 104.50 | 104.50 | 104.50 |
| Colloidal silicon dioxide | 2.75 | 2.75 | 2.75 | 2.75 | 2.75 |
| Hypromellose E5 | 5.60 | 5.67 | 5.73 | 5.79 | 5.85 |
| Citric acid monohydrate | 5.60 | 17.19 | 23.16 | 29.25 | 61.80 |
| Sodium Stearyl Fumarate | 2.80 | 2.87 | 2.90 | 2.93 | 3.09 |
| Total | 561 | 573 | 579 | 585 | 618 |

Remarks: The purified water in 1 is removed during fluidized bed granulation and drying.

TABLE 32

Dissolution data of tablet samples with different amounts of citric acid monohydrate

| | 5 min | 10 min | 15 min | 20 min | 30 min | 45 min | 60 min |
|---|---|---|---|---|---|---|---|
| Formulation 21 pH = 6.79 | 30 ± 2.31 | 55 ± 2.52 | 76 ± 1.73 | 87 ± 1.53 | 87 ± 2.52 | 85 ± 5.03 | 81 ± 3.21 |
| Formulation 22 pH = 6.78 | 33 ± 1.15 | 60 ± 1.53 | 80 ± 1.53 | 91 ± 1.15 | 94 ± 0.58 | 91 ± 1.15 | 91 ± 1.53 |
| Formulation 23 pH = 6.81 | 31 ± 1.73 | 59 ± 0.58 | 79 ± 1.00 | 91 ± 0.58 | 94 ± 0.58 | 92 ± 1.00 | 91 ± 1.53 |
| Formulation 24 pH = 6.80 | 31 ± 2.31 | 60 ± 2.65 | 80 ± 1.53 | 91 ± 0.58 | 92 ± 1.15 | 90 ± 1.53 | 86 ± 2.08 |
| Formulation 25 pH = 6.82 | 31 ± 2.52 | 60 ± 2.89 | 78 ± 4.04 | 91 ± 2.52 | 95 ± 1.53 | 94 ± 0.00 | 92 ± 0.00 |

The above data shows that when different amounts of organic acids (1%-10%, w/w) are added to the formulations, the dissolution of prepared plain tablets in the pH 6.8 medium is relatively stable, and no obvious downward trend appears.

Example 17

According to the formulations in Table 33, the dry granules were prepared according to the process of Example 14, then the prescribed amounts of hypromellose, citric acid monohydrate and sodium stearyl fumarate were added, mixed uniformly, and compressed into tablets. According to the dissolution method in Comparative Example 1, the dissolution of 40 mg strength samples in pH 6.8 medium was measured. The specific results are shown in Table 34.

TABLE 33

Formulations of tablets with different amounts of hypromellose and citric acid monohydrate (Unit: g)

| Component | Formulation 26 | Formulation 27 | Formulation 28 |
|---|---|---|---|
| Vilazodone hydrochloride | 40.00 | 40.00 | 40.00 |
| HP-β-CD | 400.00 | 400.00 | 400.00 |
| Purified water[1] | 400.00 | 400.00 | 400.00 |
| Microcrystalline cellulose | 104.50 | 104.50 | 104.50 |
| Colloidal silicon dioxide | 2.75 | 2.75 | 2.75 |
| Hypromellose E5 | 30.00 | 17.55 | 30.00 |
| Microcrystalline cellulose | 17.90 | — | — |
| Citric acid monohydrate | — | 17.55 | 17.90 |
| Sodium stearyl fumarate | 2.85 | 2.65 | 2.85 |
| Total | 598 | 585 | 598 |

The purified water in 1 is removed during fluidized bed granulation and drying.

TABLE 34

Dissolution data of tablet samples with different amounts of hypromellose and citric acid monohydrate

| | 5 min | 10 min | 15 min | 20 min | 30 min | 45 min | 60 min |
|---|---|---|---|---|---|---|---|
| Formulation 26 | 25 ± 1.73 | 45 ± 3.51 | 62 ± 4.58 | 73 ± 2.65 | 85 ± 2.89 | 85 ± 1.53 | 83 ± 1.73 |
| Formulation 27 | 30 ± 0.58 | 55 ± 1.00 | 73 ± 1.53 | 85 ± 1.53 | 89 ± 1.53 | 88 ± 1.15 | 85 ± 1.00 |
| Formulation 28 | 27 ± 3.06 | 51 ± 3.61 | 69 ± 5.03 | 81 ± 4.58 | 92 ± 2.08 | 92 ± 0.58 | 90 ± 1.53 |

The above data shows that the tablets prepared by using different amounts of hypromellose and citric acid monohydrate have relatively stable dissolution in the pH 6.8 medium, and the dissolution platform does not drop significantly at 60 minutes.

Example 18

According to the formulations in Table 35, the prescribed amount of hydroxypropyl-β-cyclodextrin was added to purified water, stirred to dissolve, then vilazodone hydrochloride was added, heated to 85° C. and stirred until the solution was clear to obtain an inclusion complex solution. Then heat was stopped, hypromellose E5 and citric acid monohydrate were added and stirred to dissolve to obtain a mixture solution. The mixture solution was sprayed on the bottom material (microcrystalline cellulose and colloidal silicon dioxide) in a fluidized bed granulator, granulated to obtain dry granules; then sodium stearyl fumarate and/or hypromellose was added, mixed well, and compressed into tablets. According to the dissolution method in Comparative Example 1, the dissolution of 40 mg strength samples in pH 6.8 medium was measured. The specific results are shown in Table 36.

TABLE 35

Formulations of tablets with different amounts of hypromellose (Unit: g)

| Component | Formulation 29 | Formulation 30 |
|---|---|---|
| Vilazodone hydrochloride | 40.00 | 40.00 |
| HP-β-CD | 360.00 | 360.00 |
| Hypromellose E5 | 5.50 | 5.50 |
| Citric acid monohydrate | 16.50 | 16.50 |
| Purified water[1] | 360.00 | 360.00 |
| Microcrystalline cellulose | 106.00 | 106.00 |
| Colloidal silicon dioxide | 2.75 | 2.75 |
| Sodium stearyl fumarate | 2.25 | 2.75 |
| Hypromellose E5 | — | 16.50 |
| Total | 533 | 550 |

Remarks: The purified water in 1 is removed during fluidized bed granulation and drying.

TABLE 36

Dissolution data of tablet samples with different amounts of hypromellose

| | 5 min | 10 min | 15 min | 20 min | 30 min | 45 min | 60 min | 90 min | 120 min |
|---|---|---|---|---|---|---|---|---|---|
| Formulation 29 | 19 ± 1.53 | 37 ± 1.53 | 53 ± 1.00 | 66 ± 1.15 | 83 ± 3.06 | 94 ± 0.58 | 95 ± 1.00 | 94 ± 0.58 | 94 ± 1.00 |
| Formulation 30 | 19 ± 0.58 | 36 ± 0.58 | 51 ± 0.58 | 63 ± 0.58 | 81 ± 0.58 | 94 ± 0.58 | 96 ± 1.15 | 95 ± 1.15 | 94 ± 0.58 |

The above data shows that when the stabilizing agent hypromellose and the acid reagent citric acid monohydrate are added to the inclusion complex solution for granulation, and then compressed, the resulting tablets have a relatively high and stable dissolution platform in the pH 6.8 medium, and no significant decrease occurs at 120 minutes. In addition, the process of adding the stabilizing agent and acid reagent to the inclusion complex solution for granulation is smoother, simpler and more feasible than the external process.

Example 19

(1) Tablets Preparation

According to the formulation in Table 37, the dry granules were prepared according to the process of Example 14, and then the prescribed amounts of hypromellose and sodium stearyl fumarate were added, mixed well, and compressed into tablets. According to the dissolution method in Comparative Example 1, the dissolution of 10 mg strength samples in various mediums was determined respectively. The specific results are shown in Table 38.

TABLE 37

Formulation of tablets (Unit: g)

| Component | Formulation 31 |
| --- | --- |
| Vilazodone hydrochloride | 40.00 |
| HP-β-CD | 400.00 |
| Purified Water [1] | 400.00 |
| Microcrystalline cellulose | 104.50 |
| Colloidal silicon dioxide | 2.75 |
| Hypromellose E5 | 5.55 |
| Sodium stearyl fumarate | 2.20 |
| Total | 555 |

Remarks: The purified water in 1 is removed during fluidized bed granulation and drying.

TABLE 38

Dissolution data of tablet samples (10 mg strength) in various mediums

| Medium | 5 min | 10 min | 15 min | 20 min | 30 min | 45 min | 60 min |
| --- | --- | --- | --- | --- | --- | --- | --- |
| 0.1N HCl | 55 ± 14.15 | 82 ± 4.73 | 93 ± 3.79 | 95 ± 5.51 | 96 ± 5.77 | 96 ± 6.08 | 96 ± 6.08 |
| pH 4.5 | 47 ± 15.31 | 81 ± 16.20 | 98 ± 2.65 | 97 ± 4.36 | 98 ± 4.36 | 98 ± 4.04 | 98 ± 4.36 |
| pH 6.8 | 50 ± 2.65 | 84 ± 3.51 | 95 ± 2.08 | 97 ± 2.08 | 97 ± 2.00 | 96 ± 3.06 | 94 ± 1.53 |

(2) Experiments with Animals

Ten beagle dogs were randomly divided into two groups in double crossover experiments under fasted and fed conditions. Each dog was given a tablet (10 mg strength) of Formulation 31 orally, and whole blood samples were taken at 0.25, 0.5, 1, 2, 4, 6, 8, 10, and 24 hours respectively. Plasma samples were prepared as follows: whole blood 200 μL to 400 μL was placed in a centrifuge tube, $K_2EDTA$ was added as an anticoagulant, and centrifuged for 60 minutes. The plasma samples were kept at −70° C. The concentration of vilazodone in the blood plasma was measured by a validated LC-MS/MS method and pharmacokinetic parameters were assessed with non-compartment model using WinNonlin 6.3 software. The results are shown in Table 39. The plasma concentration-time curve is shown in FIG. 1. Among them, $C_{max}$ represents the highest concentration of the active ingredient in plasma; $T_{max}$ represents the time when the active ingredient reaches the highest concentration in plasma; $AUC_{last}$ represents the area under the drug-time curve from the beginning of sampling to the last time point.

TABLE 39

Pharmacokinetic parameters in fasted and fed dogs

| Pharmacokinetic parameters (n = 5) | | $T_{max}$ (h) | $C_{max}$ (ng/ml) | $AUC_{last}$ (h*ng/ml) |
| --- | --- | --- | --- | --- |
| Fasted | Mean | 0.85 | 78.50 | 235.00 |
| | CV % | 55.8 | 35.1 | 40.7 |
| Fed | Mean | 2.10 | 50.20 | 218.00 |
| | CV % | 69.00 | 50.4 | 50.4 |

As shown in Table 39, the $AUC_{last}$ and the $C_{max}$ of the tablets of Formulation 31 under fasted conditions are higher than that under fed conditions, achieving the purpose of improving the bioavailability under fasted conditions. And the $AUC_{last}$ under fasted conditions is basically equivalent to that under fed conditions, indicating that the compositions provided by the present invention can be taken under fasted and fed conditions, and have basically the same therapeutic effect. Referring to Example 10, the $C_{max}$ of RLD (Reference Listed Drug) under fasted conditions is only about 32.1% of the $C_{max}$ under fed conditions and the $AUC_{last}$ of RLD under fasted conditions is only about 41% of the $AUC_{last}$ under fed conditions, the RLD has a serious food effect. Therefore, the compositions or formulations provided by the present invention can significantly improve the oral bioavailability of vilazodone under fasted conditions and reduce the influence of food effects, thereby they can be taken under fasted and fed conditions, and have basically the same curative effect, which significantly improves the compliance of patients with medication.

The solutions and methods of the present invention have been described through the preferred embodiments. It is obvious that relevant persons can make appropriate alterations, changes or combinations of the solutions, methods and applications described herein within the content and scope of the present invention to realize and apply the technology of the present invention. Those skilled in the art can learn from the content of this article and appropriately improve relevant parameters. In particular, it should be pointed out that all similar replacements and modifications are obvious to those skilled in the art, and they are all considered to be included in the present invention.

What is claimed is:

1. A composition comprising an active ingredient contained in an inclusion material, wherein the active ingredient is vilazodone or a pharmaceutically acceptable salt thereof, the inclusion material is hydroxypropyl-β-cyclodextrin, and the weight ratio of the active ingredient to the inclusion material is from 1:5 to 1:45.4.

2. The composition of claim 1, wherein the weight ratio of the active ingredient to hydroxypropyl-β-cyclodextrin is from 1:6.5 to 1:45.4.

3. The composition of claim 1, wherein the weight ratio of the active ingredient to hydroxypropyl-β-cyclodextrin is from 1:7 to 1:20.

4. The composition of claim 1, wherein the weight ratio of the active ingredient to hydroxypropyl-β-cyclodextrin is from 1:8 to 1:10.

5. The composition of claim 1, wherein the weight ratio of the active ingredient to hydroxypropyl-β-cyclodextrin is 1:9.

6. The composition of claim 1, further comprising a stabilizing agent, optionally comprising an acid reagent.

7. The composition of claim 6, wherein the stabilizing agent is a water-soluble polymer.

8. The composition of claim 7, wherein the water-soluble polymer comprises at least one selected from a group consisting of a vinylpyrrolidone based copolymer, a methacrylic acid based copolymer, a hydroxyalkylcellulose, a hydroxyalkylalkylcellulose, a cellulose phthalate, and a cellulose succinate.

9. The composition of claim 7, wherein the water-soluble polymer comprises at least one selected from a group consisting of polyvinylpyrrolidone, copovidone, hypromellose, carboxymethyl cellulose sodium, hypromellose succinate, and hypromellose acetate succinate.

10. The composition of claim 7, wherein the water-soluble polymer is hydroxypropylmethylcellulose.

11. The composition of claim 6, based on the total weight of the composition, wherein the composition comprises 0.1% to 10% stabilizing agent, optionally comprises 1% to 10% acid reagent.

12. The composition of claim 6, wherein the composition comprises an acid reagent.

13. The composition of claim 12, wherein the acid reagent comprises at least one selected from a group consisting of an organic acid, a water-soluble acidic amino acid, a water-soluble inorganic acid and an acid salt.

14. The composition of claim 13, wherein the organic acid comprises at least one selected from a group consisting of citric acid, citric acid monohydrate, D-tartaric acid, L-tartaric acid, D-malic acid, L-malic acid, fumaric acid, maleic acid, succinic acid, oxalic acid and ascorbic acid.

15. The composition of claim 12, wherein the acid reagent is citric acid and/or citric acid monohydrate.

16. The composition of claim 12, wherein the composition comprises 1% to 10% acid reagent, based on the total weight of the composition.

17. The composition of claim 1, comprising hydroxypropylmethylcellulose, and at least one of citric acid and citric acid monohydrate.

18. The composition of claim 6, further comprising one or more pharmaceutically acceptable excipients.

19. The composition of claim 18, wherein the pharmaceutically acceptable excipient includes one or more of fillers, disintegrants, and lubricants.

20. The composition of claim 18, based on the total weight of the composition, comprising 0.1% to 10% hydroxypropylmethylcellulose, optionally 1% to 10% citric acid and/or citric acid monohydrate.

21. A method for preparing the composition of claim 6, comprising mixing vilazodone or a pharmaceutically acceptable salt thereof and hydroxypropyl-β-cyclodextrin to form the inclusion complex, then adding the stabilizing agent and optionally adding an acid reagent.

22. The method of claim 21, wherein the method comprises:
1) Mixing vilazodone or a pharmaceutically acceptable salt thereof, hydroxypropyl-β-cyclodextrin and water to form the inclusion complex under heating;
2) Mixing the stabilizing agent and optional an acid reagent with the inclusion complex to obtain a mixture;
3) Solidifying the mixture and optional a pharmaceutically acceptable excipient into particles by fluidized bed or spray drying;
4) Optionally mixing the particles and other pharmaceutically acceptable excipients, and forming a formulation.

23. The method of claim 22, wherein the temperature of heating is from 80° C. to 90° C.

24. A method for treating a patient in need comprising orally administering to said patient a therapeutically effective amount of the composition of claim 18.

* * * * *